(12) United States Patent
Kim et al.

(10) Patent No.: US 10,023,627 B2
(45) Date of Patent: Jul. 17, 2018

(54) VASCULAR ENDOTHELIAL GROWTH FACTOR FUSION PROTEIN

(71) Applicant: KOREA PRIME PHARM CO., LTD., Gwangju (KR)

(72) Inventors: Daeik Kim, Gwangju (KR); Inra Seo, Jeollabuk-do (KR)

(73) Assignee: KOREA PRIME PHARM CO., LTD., Gwangju (KR)

( * ) Notice: Subject to any disclaimer, the term of this patent is extended or adjusted under 35 U.S.C. 154(b) by 0 days.

(21) Appl. No.: 15/495,358

(22) Filed: Apr. 24, 2017

(65) Prior Publication Data

US 2017/0305996 A1  Oct. 26, 2017

(30) Foreign Application Priority Data

Apr. 26, 2016 (KR) .................. 10-2016-0051152

(51) Int. Cl.

| | |
|---|---|
| *C12P 21/04* | (2006.01) |
| *C07K 14/71* | (2006.01) |
| *A61K 38/18* | (2006.01) |
| *A61K 39/395* | (2006.01) |
| *C07K 14/705* | (2006.01) |
| *A61K 38/00* | (2006.01) |
| *C07K 14/00* | (2006.01) |

(52) U.S. Cl.
CPC ............. *C07K 14/71* (2013.01); *A61K 38/18* (2013.01); *A61K 39/395* (2013.01); *C07K 14/705* (2013.01); *A61K 38/00* (2013.01); *C07K 14/00* (2013.01); *C07K 2319/00* (2013.01)

(58) Field of Classification Search
None
See application file for complete search history.

(56) References Cited

U.S. PATENT DOCUMENTS

2008/0242587 A1  10/2008  Kim et al.

FOREIGN PATENT DOCUMENTS

| JP | 5737826 B2 | 6/2015 |
| KR | 20140043313 A | 4/2014 |

OTHER PUBLICATIONS

Carmeliet et al., "Angiogenesis in Cancer and other Diseases", Nature, vol. 407, pp. 249-257, Sep. 14, 2000.
Kuwano et al., "Angiogenesis Factors", Internal Medicine, vol. 40, Issue 7, pp. 565-572, Jul. 2001.
Youssoufian et al., "Review:Monoclonal Antibodies to the Vascular Endothelial Growth Factor Receptor-2 in Cancer Therapy", Clinical Cancer Research, vol. 13, Issue 18, pp. 5544s-5548s, Sep. 15, 2007.
Ellis et al., "VEGF-Targeted Therapy: Mechanisms of Anti-Tumour Activity", Nature Reviews Cancer, vol. 8, pp. 579-591, Aug. 2008.
Lee et al., "Novel Glycosylated VEGF Decoy Receptor Fusion Protein, VEGF-Grab, Efficiently Suppresses Tumor Angiogenesis and Progression", Molecular Cancer Therapeutics, vol. 14, Issue 2, pp. 470-479, Feb. 2015.

*Primary Examiner* — Sean E Aeder
(74) *Attorney, Agent, or Firm* — Moser Taboada

(57) ABSTRACT

The present invention relates to a fusion protein binding to a vascular endothelial growth factor (VEGFR) and/or a placental growth factor (PlGF). The fusion protein of the present invention comprises (a) a Fc domain of IgG1, wherein two heavy chains are linked by disulfide bond, and (b) four immunoglobulin domain2s of the VEGFR1, wherein two immunoglobulin domain2s are sequentially fused to each heavy chain of the Fc domain of (a). The present fusion protein has excellent activities of inhibiting cell migration and cell invasion, and has highly enhanced growth inhibition effects to various carcinomas and fibroblasts. Therefore, The fusion protein of the present invention can be used in the preparation of an agent for treating cancers or ocular diseases.

17 Claims, 24 Drawing Sheets

| | Construct Name | Diagrams |
|---|---|---|
| 1 | VEGFR2-VEGFR2-FC(KP-VR1) |  |
| 2 | VEGFR1-VEGFR1-FC(KP-VR2) |  |
| 3 | VEGFR2-VEGFR1-FC(KP-VR3) |  |
| 4 | VEGFR1-VEGFR2-FC(KP-VR4) |  |

PGKp: PGK(phosphoglycerate kinase) promoter
DHFR: DHFR(dihydrofolate reductase) gene
SV40pA: SV40 polyadenylation signal
EF2/CMVp: EF2/CMV hybrid promoter
pac: Puromycin resistance gene
pMB1ori: pMB1 origin of replication
Aph: Kanamycin resistance gene

VASCULAR ENDOTHELIAL GROWTH FACTOR FUSION PROTEIN

CROSS-REFERENCE TO RELATED APPLICATIONS

The present disclosure claims the benefit of Korean Patent Application No. 10-2016-0051152 filed Apr. 26, 2016, which is incorporated herein by reference in its entirety for all purposes.

FIELD

The present invention relates to a vascular endothelial growth factor receptor (VEGFR) fusion protein which is used in the preparation of an agent for treating cancers or ocular diseases. The fusion protein of the present invention is a multivalent bispecific antibody, wherein VEGFR extracellular domain is fused to Fc region of immunoglobulin-like domain.

BACKGROUND

A vascular endothelial growth factor (VEGF) is a signaling protein which plays an important role in promoting both vasculogenesis and angiogenesis. The VEGF functions as a part of the system which restores and supplies oxygen to tissues, when blood circulation is inadequate. The well-known function of the VEGF is to create new blood vessels during embryonic development, at the injured site, in muscle following exercise, and in the formation of vessels to bypass blocked vessels.

The increased amount of VEGFs, however, may cause abnormal angiogenesis. In particular, the angiogenesis is related to tumor development such that it is involved in primary or metastatic tumor generation. Further, cancer metastasis occurs when a primary cancer cell is introduced into blood vessel by the angiogensis. It is reported that the angiogenesis causes, for example, asthma, difficulty in breathing, endometriosis; acute and chronic inflammation, such as, atherosclerosis and tissue edema; infectious disease, such as, hepatitis and Kaposi's sarcoma; autoimmune disease, such as, diabetes, psoriasis, rheumarthritis and thyroiditis; and other diseases comprising diabetic retinopathy, choroidal neovascularization (CNV), age-related macular degeneration (AMD), angiofibroma, and etc. (Carmeliet, P. y Jain, R K. 2000. Nature 407: 249-257; Kuwano M, et al. 2001. Intern Med 40: 565-572).

The VEGF, which plays an important role in angiogenesis, influences mainly on the vessel endothelium cells. In accordance with in vitro test, the VEGF stimulates division and wandering of the endothelial cells, and increases capillary vessel permeability as well.

In mammals, VEGF is classified into 5 types, such as, VEGF-A, VEGF-B, VEGF-C, VEGF-D and PlGF (placenta growth factor). The VEGF-A stimulates angiogenesis, endothelial cell wandering, division, blood vessel lumen formation, chemotaxis of macrophage and granulocyte, and blood vessel expansion. The VEGF-B promotes embryonic angiogenesis, in particular, the development of myocardial tissues. The VEGF-C accelerates lymphangiogenesis, and the VEGF-D is necessary for the growth of lymphatic vessels which enclose the lung bronchioles. Further, the PlGF is important for angiogenesis in the vasculogenesis, ischemia, inflammation, injury recovery, and cancer.

The VEGF receptor (VEGFR), a receptor whose ligand is VEGF, consists of 3 subtypes (VEGFR1 (flt-1), VEGFR2 (Kdr/flk-1) and VEGFR3 (flt-4)), and exists in the form of membrane-bound VEGFR (mbVEGFR) or soluble VEGFR (sVEGFR) through the alternative splicing of genes.

The VEGFR is expressed in neurons, Kaposi's sarcoma, and hematopoietic stem cells, while it is usually found in endothelial cells. Once the VEGF binds to VEGFR, signals are transferred by dimerization of the receptor and phosphorylation of the receptor tyrosine residues.

The VEGF binds to its receptors, VEGFR1 and VEGFR2, with high affinity and transfers signals mainly through the VEGFR2, and induces the mechanism of angiogenesis comprising growth and migration of endothelial cells.

Therefore, VEGF and VEGFR2 have been studied as targets for inhibiting or suppressing angiogenesis induced by the VEGF (Ellis and Hicklin, Nature Rev. Cancer, 8:579, 2008; Youssoufian et al., Clin. Cancer Res., 13:5544s, 2007).

The bispecific antibody or multi-specific antibody reported in the previous studies includes i) Conbercept consisting of VEGFR1 domain2, VEGFR2 domain 3, domain4 and IgG1 Fc, ii) VEGF-Trap (aflibercept) consisting of VEGFR1 domain2, VEGFR2 domain3 and IgG1 Fc, and iii) VEGF-Grab consisting of VEGFR1 domain2, domain3 and IgG1 Fc.

We, inventors, have studied eagerly to develop a multi-specific antibody for treating cancers and ocular diseases by suppressing or inhibiting angiogenesis, and have surprisingly found that the fusion protein construct of immunoglobulin-like domain of the present invention binds to VEGF-A and PlGF with both high sensitivity and specificity, and has significantly excellent effects of inhibiting proliferation, growth and/or angiogenesis of various tumors.

The teachings of all patents, published applications and references cited herein are incorporated by reference in their entirety.

SUMMARY

Technical Problem

Accordingly, the purpose of the present invention is to provide a recombinant fusion protein for treating cancers and/or ocular diseases caused by angiogenesis.

Another purpose of the present invention is to provide nucleic acids, recombinant vectors comprising the nucleic acids, and host cells for expressing the recombinant vectors.

Another purpose of the present invention is to provide a pharmaceutical composition comprising the recombinant fusion proteins expressed by the host cells to prevent or treat cancers and/or ocular diseases.

Technical Solution

In order to solve the technical problems, the present invention provides a VEGFR fusion protein of 4 valent multi-specific antibody. The fusion protein of the present invention, which is a recombinant fusion protein of immunoglobulin-like domain, comprises (a) a Fc domain of IgG1, wherein two heavy chains are linked by disulfide bond, and (b) four immunoglobulin domain2s of the VEGFR1, wherein two immunoglobulin domain2s are sequentially fused to each heavy chain of the Fc domain of (a).

Further, the present invention provides an isolated nucleic acid molecule encoding the said recombinant fusion protein.

Further, the present invention provides a recombinant expression vector comprising the said nucleic acid molecule.

In one embodiment of the present invention, a host cell transformed with the said recombinant expression vector is provided. The recombinant expression vector is inserted into the host cell to produce transformed cells. The appropriate host cell for the recombinant expression vector may be a procaryote, for example, *E. Coli, Bacillus subtilis, Streptomyces* genus, *Pseudomonas* genus, *Proteus mirabilis* genus or *Staphylococcus* genus.

In addition, the appropriate host cell may be an eukaryotic cell including, for example, fungi, such as, *Aspergillus* genus; yeast, such as, *Pichia pastoris* genus, *Saccharomyces cerevisiae, Schizosaccharomyces* genus and *Neurospora crassa*; other lower eukaryotic cells; and higher eukaryotic cells, such as, insect cells. In addition, the eukaryotic cell may be a plant cell or a mammalian cell and, preferably, COS7 cell (monkey kidney cells), NSO cell, SP2/0 cell, CHO cell (chinese hamster ovary), W138 cell, BHK cell (baby hamster kidney cell), MDCK cell, multiple myeloma cell line, HuT78 cell and HEK293 cell can be used for the expression.

In the present invention, the method for host cell transformation comprises introducing nucleic acids into organisms, cells, tissues or organs, while the most appropriate method may be selected according to the host cell. The available transformation methods include, for example electroporation, protoplast fusion, $CaPO_4$ precipitation, $CaCl_2$ precipitation, silicon carbide fiber agitation, *agrobacterium*-mediated transformation, and PEG, dextran sulfate, lipofectamine and drying/inhibition-mediated transformation.

To express the fusion protein of the present invention, various combinations of recombinant expression vectors and host cells can be employed. The preferred expression vector for eukaryotic cells comprises gene expression regulatory sequences derived from, but not limited to, SV40, bovine papillomavirus, adenovirus, adeno-associated virus, cytomegalovirus and retrovirus.

The expression vector, which can be used for bacterial hosts, comprises bacterial plasmids, such as, pET, pRSET, pBluescript, pGEX2T, pUC vector, col E1, pCR1, pBR322, pMB9 and the derivatives thereof, obtained from *E. coli*; a plasmid having broad host range, such as, RP4; phage DNAs exemplified by various phage lambda derivatives, such as, λgt10, λgt11 and NM989; other DNA phages, such as, M13 and filamentous single-stranded DNA phage. The expression vector available for yeast cells may be a plasmid and its derivatives. The expression vector for insect cells includes pVL941. Therefore, in the present invention, the recombinant expression vector may be a plasmid, YAC (yeast artificial chromosome), YEp (yeast episomal plasmid), YIp (yeast integrative plasmid) or recombinant virus.

In one embodiment of the present invention, a method for producing the VEGFR fusion protein is provided. The method comprises, (a) incubating the host cells under conditions for producing a fusion polypeptide, (b) recovering the produced fusion polypeptide. The host cell has the recombinant expression vector in which the nucleic acid sequence encoding the fusion polypeptide is operably linked to the expression regulatory sequence.

The fusion polypeptide can be expressed by using the recombinant expression vector which comprises a nucleic acid sequence encoding (a) a first VEGFR1 immunoglobulin-like domain2; (b) a second VEGFR1 immunoglobulin-like domain2; and (c) Fc region polypeptide of human IgG, in prokaryotic or eukaryotic expression system. The obtained fusion polypeptide can be purified by the conventional methods for producing biologically stable proteins. For example, dialysis, ion-exchange chromatography, affinity chromatography, HPLC (high pressure liquid chromatography), and PAGE (polyacrylamide gel electrophoresis) can be used for this purpose, but not limited thereto.

Further, the present invention provides a VEGFR fusion protein prepared by the method above. According to the Examples 2 to 4 of the specification, the fusion proteins of the present invention have significantly increased binding affinities to the target ligands, VEGF-A and PlGF, comparing to the aflibercept and bevacizumab. Further, according to the Example 5, the fusion protein of the present invention (KP-VR2) can be used as an anti-VEGF, since it binds to the VEGF with high sensitivity and selectivity when administered to a subject in need of treatment of a disease relating to VEGF. Further, according to the Example 6, the fusion protein (KP-VR2) has pharmacokinetic profiles similar to the aflibercept, and thus it can replace the commercialized anti-VEGF or be used in combination therewith. Therefore, the fusion protein of the present invention provides a pharmaceutical composition for treating tumors and a pharmaceutical composition for treating ocular diseases caused by the angiogenesis in eye.

In the present invention, the ocular diseases relating to angiogenesis comprise, for example, age-related macular degeneration (ARMD), exudative age-related macular degeneration, choroidal neovascularization (CNV), choroidal vasculopath, pathologic myopia, diabetic retinopathy, diabetic macula edema, retinal vascular occlusions, retinopathy of prematurity (ROP) and neovascular glaucoma (NVG). Further, the choroidal neovascularization may be myopic CNV, traumatic CNV, CNV due to uveitis, ocular histoplasmosis, or idiopathic choroidal neovascularization.

Further, according to the Example 7, the fusion protein of the present invention more efficiently inhibits or suppresses migration and invasion of human umbilical vein endothelial cells (HUVEC) and Ea-hy926 (human endothelial hybrid cell line), at lower concentration. This suggests that the present fusion protein can be used as an effective angiogenesis inhibiting agent for treating diseases including cancers and angiogenic ocular diseases, since cell migration and invasion are important in the progression of the vasculogenesis of endothelial cells.

Further, the Examples 8 to 10 support that the present fusion protein (KP-VR2) has inhibitory activity on various carcinomas and fibroblast cell lines derived from human, and inhibitory activity on their xenografts in nude mice.

In one embodiment, the tumor which can be treated by the fusion protein of present invention comprises, for example, epidermoid tumors, squamous tumors in head and neck, colorectal tumor, prostate cancer, breast cancer, lung cancer (including small cell lung cancer and non small cell lung cancer), pancreatic cancer, thyroid cancer, ovarian cancer, liver cancer, Kaposi's sarcoma, central nervous system (CNS) abnormalities of proliferation (neuroblastoma, capillary vessel carcinoma, meningioma and brain metastasis), melanoma, kidney cancer, gastrointestinal tumor, rhabdomyosarcoma (RMS), neuroblastoma, leiomyosarcoma and etc.

The pharmaceutical composition of the present invention can be administered in separate or combination with other treatment at the same time or sequentially, according to the disease to be treated. The pharmaceutical composition of the present invention may comprise pharmaceutically acceptable excipient, buffer solution, stabilizer or pharmaceutically acceptable carrier or other materials well-known to the experts in the art. These materials are non-toxic and does not interfere nor interact with the pharmacological effects of the active ingredients, and their precise properties may depend on the administration routes, such as, oral, mucosal and parenteral (for example, intravenous). The fusion protein of the present invention can be injected with the amount of 0.001 to 5 mg/one eye, or 1~10 mg/kg.

Advantageous Effects

The VEGFR of the present invention, a 4 valent antibody, is a fusion protein of immunoglobulin-like domain, and comprises (a) an Fc domain of IgG1, wherein two heavy chains are linked by disulfide bond, and (b) four immunoglobulin domain2s of VEGFR1, wherein two immunoglobulin domain2s are sequentially fused to each heavy chain of the Fc domain of (a). The VEGFR of the present invention has significantly enhanced binding affinity to VEGF and PlGF, and has excellent inhibitory activity on the migration and invasion of endothelial cells, and inhibits the growth and proliferation of various cancers and fibroblasts. Thus, the present fusion protein can be used for the development of a pharmaceutical agent for treating cancers and ocular diseases caused by angiogenesis.

DETAILED DESCRIPTION

The present invention is generally directed to 4 valent Fc-fusion proteins, and more particularly, to Fc-fusion proteins. Fc-fusion proteins are typically formed by fusion of the Fc fragment of immunoglogulin (Ig) to a ligand-binding region of receptor and have a structure similar to that of an antibody.

A wide variety of immunoadhesion molecules are suggested in the literature. However, immunoadhesion molecules according to the present invention have different structure with the conventional immunoadhesion molecules, and there is also no prior art predicting or describing preparations of the immunoadhesion molecules according to the present invention.

Hereinafter, the present invention will be described in more detail with reference to the examples. It should be understood that these examples are not to be in any way construed as limiting the present invention.

EXAMPLES

Example 1

Production of the VEGFR Fusion Protein KP-VR2

Human VEGFR2 domain3 fused to human IgG1 Fc domain (KP-VR1); human VEGFR1 domain2 (SEQ No.: 1) fused to human IgG1 Fc domain (SEQ No.: 2) (KP-VR2); human VEGFR2 domain3 (SEQ No.: 3) and VEGFR1 domain2 fused to human IgG1 Fc domain (KP-VR3); human VEGFR1 domain 2 and VEGFR2 domain 3 fused to human IgG1 Fc domain (KP-VR4, aflibercept) were cloned into pCHO 1.0 vector (Invitrogen), respectively.

Figure 1:
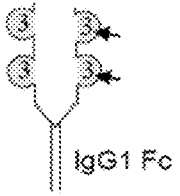
FIG. 1 illustrates fusion protein constructs including the fusion protein of the present invention and other fusion proteins of the prior arts.
Figure 1:
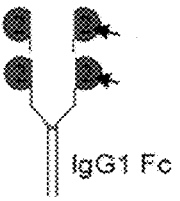
Figure 1:
Figure 1:
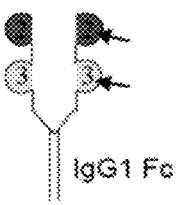
Figure 2A:
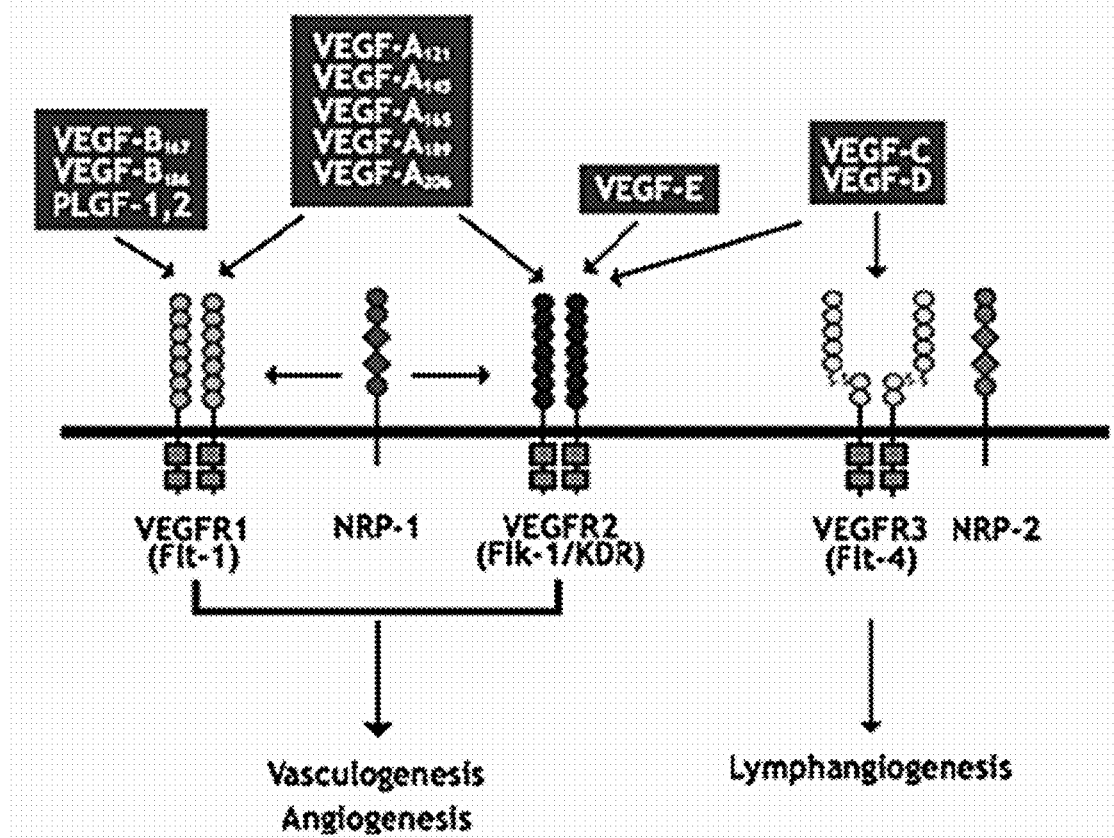
FIGS. 2A, 2B and 3 illustrate the structures of aflibercept and KP-VR2 (VEGFR fusion protein) of the present invention.
Figure 2B:
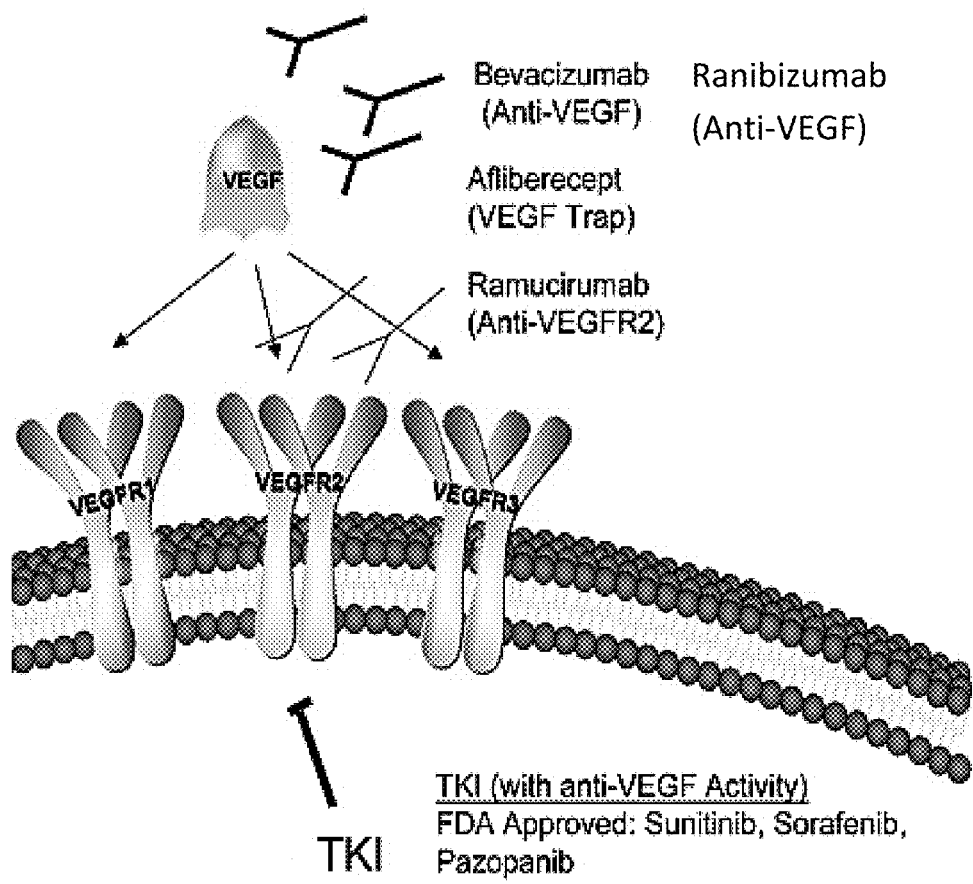
Figure 3:
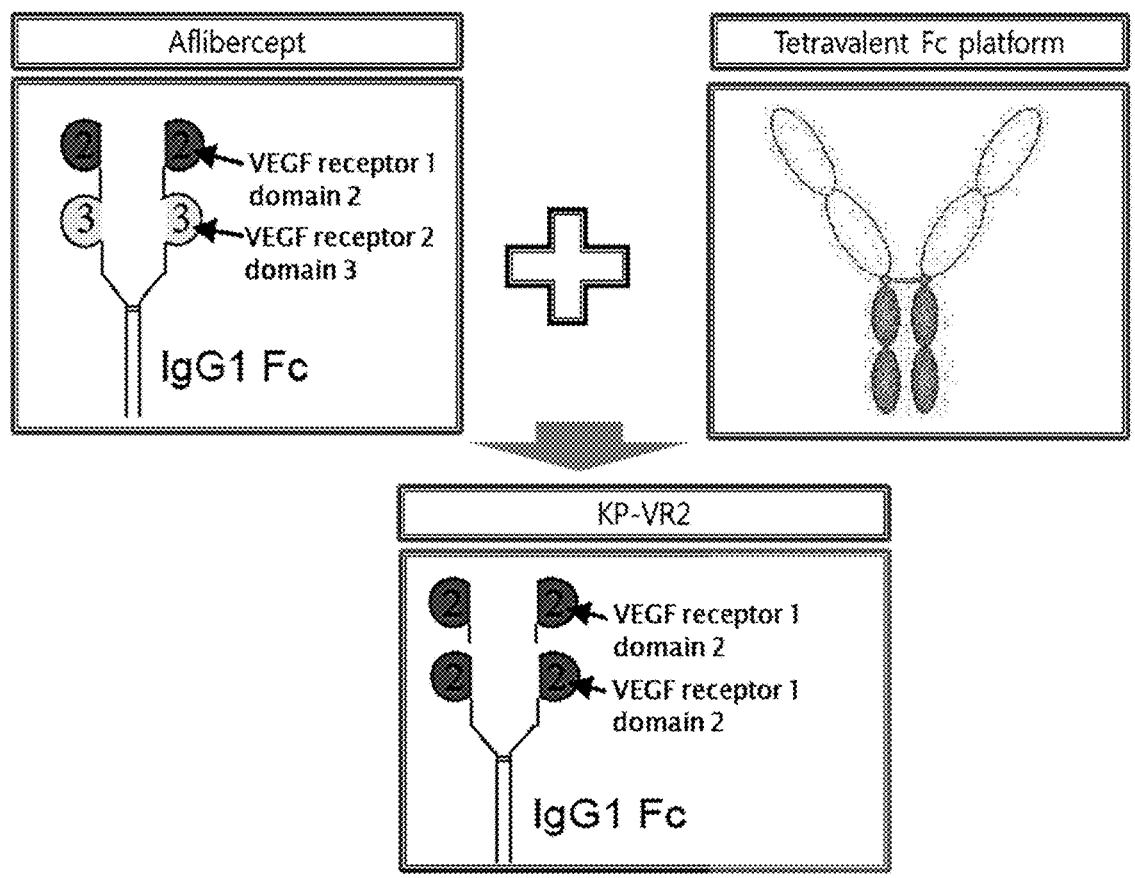
Figure 4:
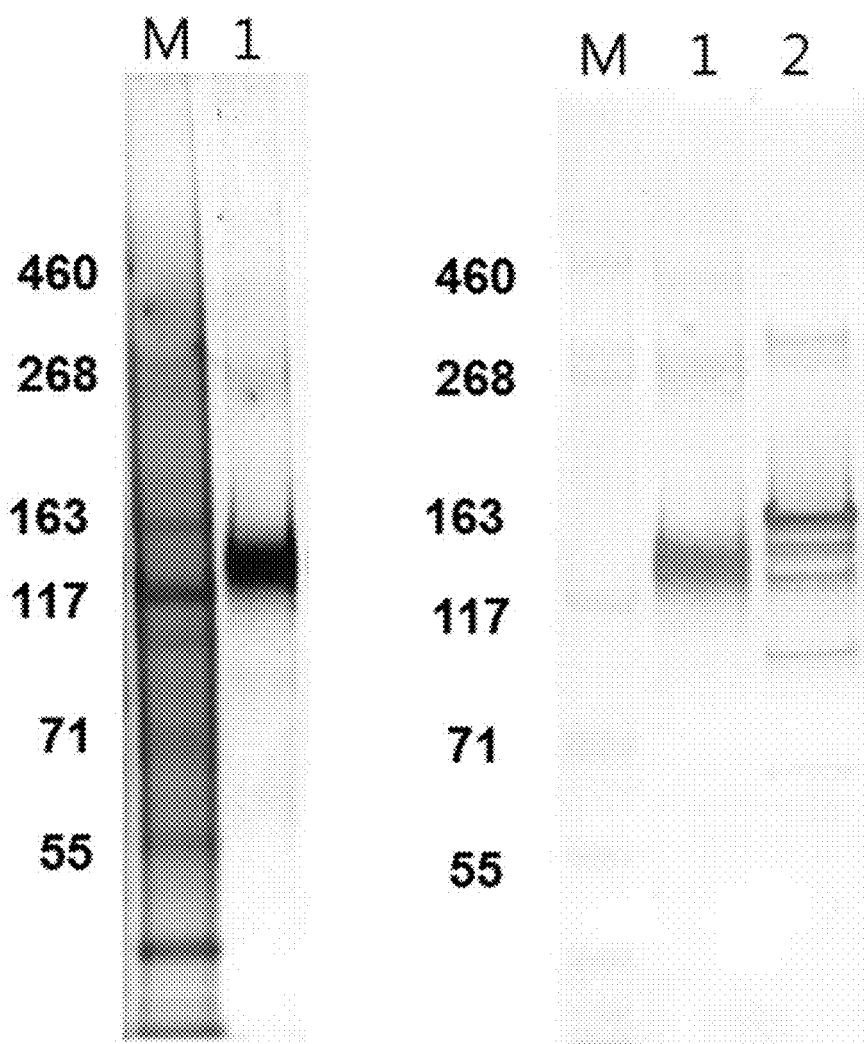
FIG. 4 shows the molecular weight of KP-VR2 fusion protein confirmed by SDS-PAGE and western blot.

The CHO-S cells (Invitrogen) were transfected with the KP-VR1, KP-VR2, KP-VR3 and KP-VR4 constructs, respectively, and the transfected cells were selected by using methotrexate and puromycin. The KP-VR2 and KP-VR4 (VEGF-Trap; aflibercept; Eylea) were purified with protein A-sepharose affinity chromatography. The purified proteins were quantified by HPLC analysis, and then SDS-PAGE and western blot were performed sequentially. The FIG. 1 shows each construct. The FIG. 3 represents the results of western blot. As shown in the FIG. 3, the human VEGFR1 domain2 fused to human IgG1 Fc domain (KP-VR2) had about 120 kDa band size.

Example 2

Figure 5:
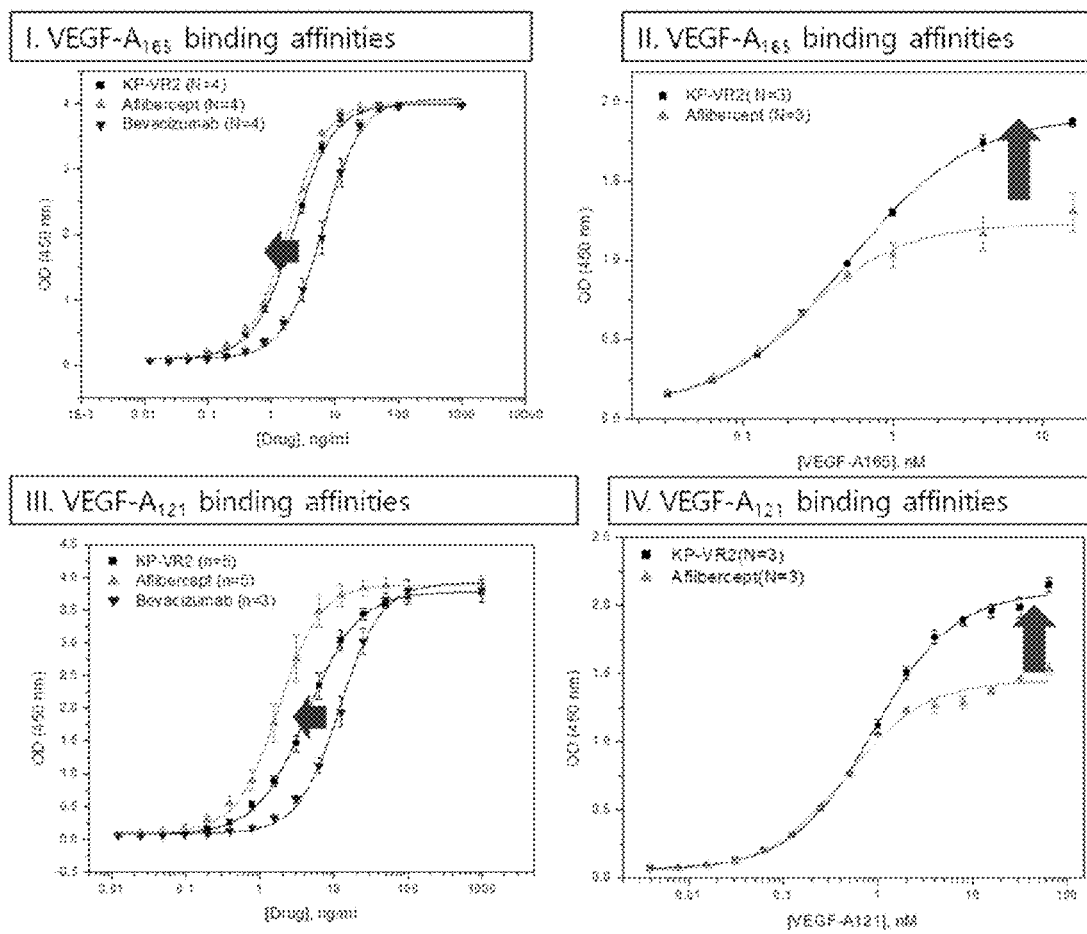
FIG. 5 shows binding affinities of the fusion protein of the present invention, aflibercept and bevacizumab for VEGF-A165 or VEGF-A121.

Determination of Binding Affinities of the KP-VR2 of the Present Invention, Aflibercept and Bevacizumab to VEGF-A The binding affinities of the KP-VR2 of the present invention, aflibercept and bevacizumab to VEGF-A were compared in this experiment. ELISA assay was carried out in accordance with the BEVACIZUMAB Summary Validation Report (Feb. 28, 2014). The 96 well plate (Nunc) was coated with 50 ng/ml VEGFA165(I) or VEGFA121(III) (R&D systems), and then KP-VR2, KP-VR4 (aflibercept) or Avastin (bevacizumab) was added to the well in gradually increasing amount from 0.0122 to 1,000 ng/ml. Next, the plate was washed and reacted with peroxidase-conjugated anti-human Fc antibody. Then, 3,3,5,5-tetramethylbenzidine (TMB) solution (Roche) was added, and thereafter absorbance was detected at 450 nm by using ELISA reader (spectrophotometer, Biorad). The FIGS. 5 (I and III) shows the results.

Furthermore, the 96 well plate was coated with 2 nM of KP-VR2 or KP-VR4 (aflibercept), and then VEGF165(II) or VEGF121(IV) (R&D systems) was added thereto in gradually increasing amount from 0.03125 to 64 nM, to compare the binding amount of KP-VR2 or KP-VR4 (aflibercept) to VEGF-A. Next, the plate was washed and reacted with the anti-human VEGF antibody for 1 hour. Then, the plate was washed again and reacted with peroxidase-conjugated anti-goat Ig antibody. Next, 3,3,5,5-tetramethylbenzidine solution was added, and thereafter absorbance was detected at 450 nm by using ELISA reader (spectrophotometer, Biorad). The FIGS. 5 (II and IV) shows the results.

Example 3

Comparison of Neutralization Activity for PLGF (Placental Growth Factor) of the KP-VR2 of the Present Invention, Aflibercept or Bevacizumab ELISA was performed for the detection of binding affinities of the KP-VR2 of the present invention, aflibercept or bevacizumab to PIGF (placental growth factor). The 96 well plate was coated with 50 ng/ml of PIGF(I), and then KP-VR2 (0.0122~1,000 ng/ml KP-VR4 (aflibercept) (0.390625~16,000 ng/ml) or Avastin (bevacizumab) (0.0122~1,000 ng/ml) was added to the well in gradually increasing amount. Then, the plate was washed and reacted with peroxidase-conjugated anti-human Fc antibody. Next, 3,3,5,5-tetramethylbenzidine solution was added, and absorbance was detected at 450 nm by using ELISA reader (spectrophotometer, Biorad).

Further, the 96 well plate was coated with 400 ng/ml of KP-VR2 or KP-VR4 (aflibercept), and then PIGF was added thereto in increasing amount from 0.8 to 12,500 ng/ml, to compare the binding amount of KP-VR2 or KP-VR4 (aflibercept) to PIGF. Next, the plate was reacted with biotinylated-PIGF antibody for 1 hour, and then was washed. Thereafter, the plate was further reacted with peroxidase-conjugated anti-goat Ig antibody (R&D systems). Next, 3,3,5,5-tetramethylbenzidine (TMB) solution was added, and then absorbance was detected at 450 nm by using ELISA reader.

Further, the 96 well plate was coated with 50 ng/ml of PIGF, and then KP-VR2 or aflibercept was added thereto in gradually increasing amount from 2 to 31,250 ng/ml, to compare the binding amount of KP-VR2 and KP-VR4 (aflibercept) to PIGF. Next, the plate was washed and reacted with anti-human Fc antibody. Thereafter, 3,3,5,5-tetramethylbenzidine (TMB) solution (Roche) was added, and absorbance was detected at 450 nm by using ELISA reader. The FIGS. 6 (I, II and III) shows the results.

Figure 6:
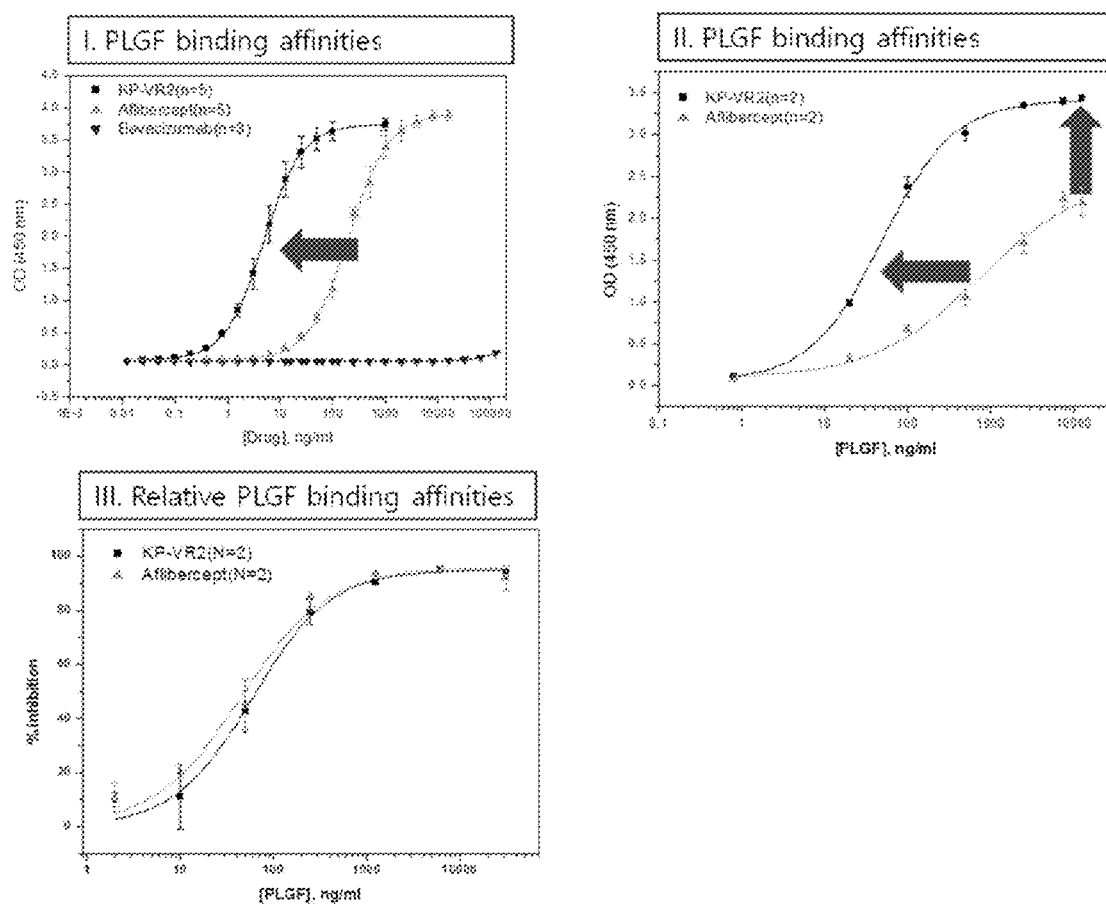
FIG. 6 shows binding affinities of the fusion protein of the present invention, aflibercept and bevacizumab for PlGF.

As shown in the FIG. 6 (I), the titer of the KP-VR2 to PIGF increased about 42 times comparing to the KP-VR4 (aflibercept), and the maximum binding amount of the KP-VR2 to PIGF increased about 54.3% in comparison to the KP-VR4 (aflibercept) (FIG. 6 (II)). These results support that the KP-VR2 has significantly higher binding affinity to the PIGF. Meanwhile, the KP-VR2 of the present invention showed similar binding affinity to the PIGF as the KP-VR4 (aflibercept).

Example 4

Comparison of Total Avidity of the Present Fusion Protein of KP-VR2 to its Ligand (VEGFA165, VEGFA121 or PLGF)

The avidity of the KP-VR2 and KP-VR4 (aflibercept) to VEGFA165, VEGFA121 or PIGF were determined by ELISA, and the results were shown in Table 1 (the comparison of avidity of KP-VR2 and aflibercept to VEGF and PIGF) below.

TABLE 1

| ligand | | ligand binding affinity Bmax (OD) | note |
|---|---|---|---|
| KP-VR2 | VEGF-A165 | 1.93 ± 0.01 | 54.4% increased |
| aflibercept | VEGF-A165 | 1.25 ± 0.05 | |
| KP-VR2 | VEGF-A121 | 2.10 ± 0.03 | 44.83% increased |
| aflibercept | VEGF-A121 | 1.45 ± 0.03 | |
| KP-VR2 | PLGF | 3.42 ± 0.02 | 54.3% increased |
| aflibercept | PLGF | 2.21 ± 0.03 | |

As shown in the Table 1, the KP-VR2 had about 45~55% higher binding affinity to VEGFA than the aflibercept, and had about 55% higher binding affinity to PIGF than the aflibercept.

Example 5

Comparison of Binding Affinities of the Present Fusion Protein of KP-VR2 and Aflibercept to VEGF-A165

The binding affinity comparison experiment using SPR (surface plasmon resonance) was carried out following the reference (Binding and neutralization of vascular endothelial growth factor (VEGF) and related ligands by VEGF Trap, ranibizumab and bevacizumab. Angiogenesis. 2012, 15(2):171-185). Firstly, SPR chip was stabilized with HBST buffer (50 nM HEPES, 150 nM NaCl, 0.1% Tween 20) and then protein A was bound thereto at a density of 1,000 RU (resonance unit). The chip was washed by using 10 mM glycine buffer, and the remaining unbound protein A was removed therefrom. Next, KP-VR2, KP-VR4 (aflibercept) and bevacizumab (2 nM) were added and bound to the chip, respectively. The VEGFA165 (0.5~8 nM) was flown over the chip. The results were shown in FIG. 7 and Table 2 (binding affinity of the KP-VR2, KP-VR4, and KP-VR3 to VEGF).

TABLE 2

| ligand | | Kinetic binding parameters Rmax (RU) | note |
|---|---|---|---|
| KP-VR2 | VEGF | 119.55 ± 6.12 | 47.5% increased |
| aflibercept | VEGF | ~87.44 | |
| avastin | VEGF | ~74.66 | |

Figure 7:
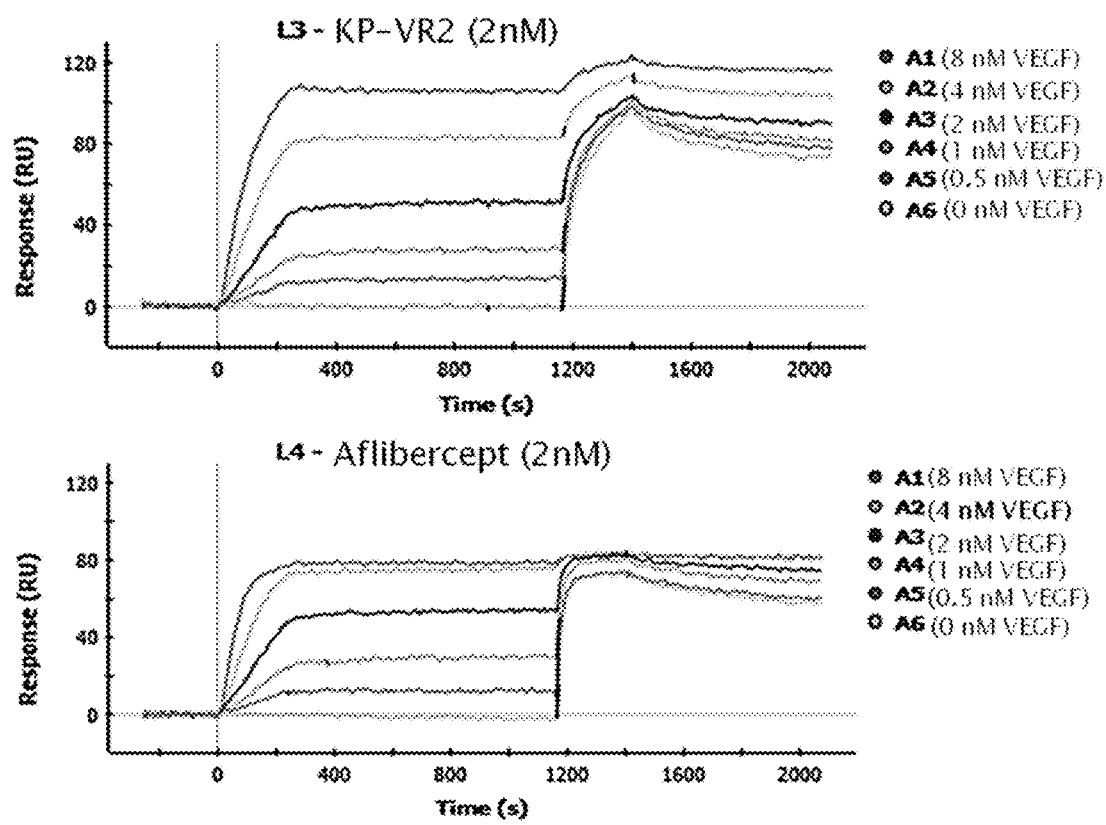
FIG. 7 shows the maximum binding interactions between the present fusion protein or aflibercept and VEGF-A165.

As shown in the FIG. 7, the amount of KP-VR2 increased in proportion to the concentration of VEGFA165, while KP-VR4 (aflibercept) and bevacizumab reached the maximum binding value at 4 nM. Further, as shown in the Table 2, the maximum binding value of KP-VR2 to VEGF-A was about 120 RU, while the maximum binding Values of KP-VR4 (aflibercept) and bevacizumab (Avastin) were 87 RU and 75 RU, respectively. Therefore, it was confirmed that the KP-VR2 of the present invention had significantly increased total avidity to VEGF-A, comparing to KP-VR4 (aflibercept) and bevacizumab.

Example 6

The Pharmacokinetic Profile of the Present KP-VR2 in a Rat

Rats were classified into two groups to assess the pharmacokinetic profiles of the VR-2 and KP-VR4 (aflibercept). 1 mg/kg of the KP-VR2 and 1 mg/kg of the KP-VR4 (aflibercept) were i.v. (intravenous) injected into one group of rats, and they were s.c. (subcutaneous) injected into another group of rats.

Figure 8A:
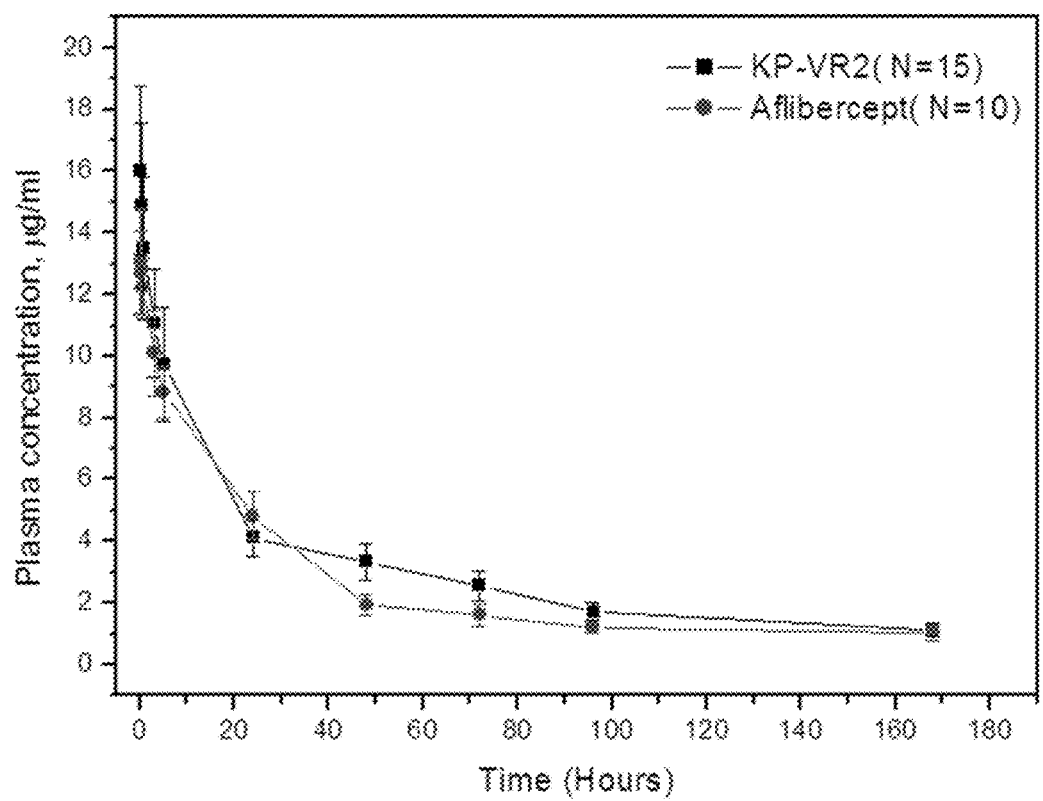
FIGS. 8A and 8B show pharmacokinetic profiles upon administration routes of the present fusion protein, comparing to aflibercept.
Figure 8B:
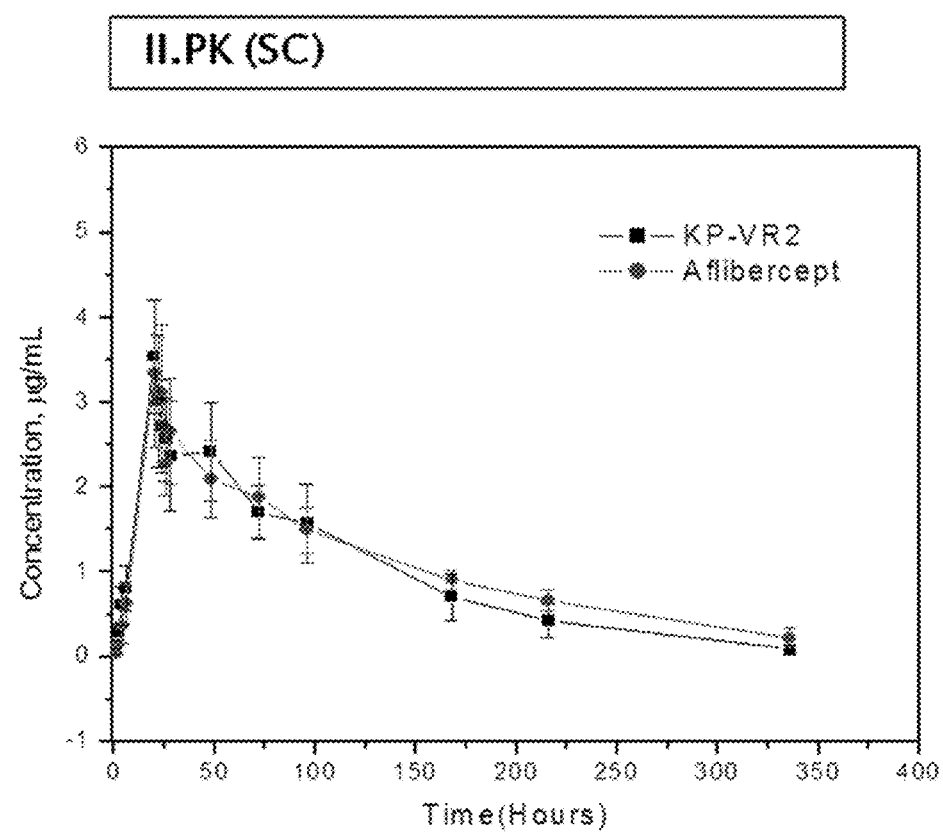

As for the i.v. injection group, the blood was gathered from the rats jugular veins at 0 min, 5 min, 15 min, 45 min, 3 hours, 5 hours, 24 hours, 48 hours, 72 hours, 96 hours and 168 hours after the respective caudal vein injection of the KP-VR2 and KP-VR4 (aflibercept) to 6 week-old female SD (Sprague-Dawley) rats weighing 180~200 g (VEGF-TRAP: A VEGF BLOCKER WITH POTENT ANTI TUMOR EFFECTS. PNAS. 2002, 99(17):139311398), and thereafter the changed amount of the injected materials was assessed. Next, as for the s.c. injection group, the blood was gathered from the rat jugular vein at 0 hour, 1 hour, 2 hours, 4 hours, 6 hours, 20 hours, 22 hours, 24 hours, 26 hours, 28 hours, 48 hours, 96 hours, 168 hours, 240 hours and 336 hours after the respective injection of the KP-VR2 and KP-VR4 (aflibercept) on the back area of the rat neck of 6 week-old female SD (Sprague-Dawley) rats weighing 180~200 g, and thereafter the changed amount of the injected materials was assessed. The results were shown in FIGS. 8A and 8B. As shown in the FIGS. 8A and 8B, the KP-VR2 showed similar in vivo half-life and pharmacokinetic profiles to the KP-VR4 (aflibercept).

Example 7

Analysis of Cell Migration and Invasion Inhibition by KP-VR2 in Endothelial Cells

Example 7-1

Detection of Cell Invasion Inhibition Induced by the VEGF-A after Treating HUVEC (Human Umbilical Vein Endothelial Cells) with the KP-VR2 and KP-VR4 (Aflibercept)

The cell migration was assessed by using chemotactic motility assay in Transwell system, to detect cell migration and invasion of endothelial cells by the KP-VR2. The growth factor reduced Matrigel (Millipore) was coated on the Transwell system, and then cell invasion was determined by using the invasion assay. The quantitative analysis of cell migration and cell invasion assay were performed as follows. The bottom of the Transwell was coated with 10 µl of 0.1% gelatin and dried for 24 hours. The QCM 24-well cell invasion assay kit (Corning) was used for this experiment. The detached cells were gathered with cell invasion assay medium (endothelial cell basal medium, EBM, 0.1% FBS). The cell number was adjusted to 5×10⁴ cells/300 µl cell invasion medium, and the cells were seeded on each insert. 6 wells were treated with 0~200 nM KP-VR2, KP-VR4 (aflibercept) (Eylea, trademark), or bevacizumab (Avastin, trademark). The VEGFs (350 ng/ml) in the 6 wells were treated and then incubated for 48 hours at 37 ⌞. After the incubation, the remaining cells and medium were removed and the insert was moved to a new well. Next, the insert was placed in 225 µl of the cell isolation solution and further incubated for 30 minutes, at 37 ⌞ in an incubator.

The insert was stirred to detach the remaining cells. Thereafter, 75 µl of the lysis buffer/dye solution was further added to the mixed solution of the cell isolation solution and the cells, and the resulting solution was placed for 15 minutes at room temperature. Next, 200 µl of the solution was moved into 96 well and 595 nm fluorescence image was obtained. The results were shown in the FIGS. 9A and 9B and Table 3 (the analysis of the inhibition of endothelial cell migration and invasion by KP-VR2).

TABLE 3

| VEGF inhibitor | ligand | endothelial cell migration inhibition rate IC$_{50}$ (nM) | note |
|---|---|---|---|
| KP-VR2 | VEGF-A$_{165}$ | 11.00 ± 1.40 | |
| aflibercept | VEGF-A$_{165}$ | 20.08 ± 3.95 | |
| bevacizumab | VEGF-A$_{165}$ | 21.28 ± 2.72 | |

Figure 9A:
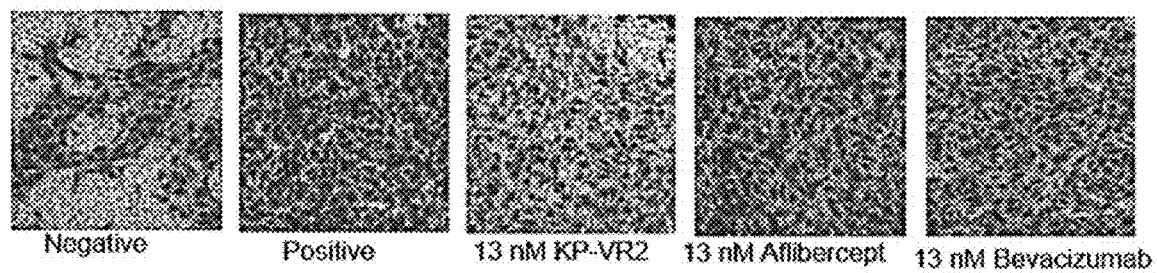
FIGS. 9A and 9B show the effects of the fusion protein of the present invention, aflibercept and bevacizumab on HUVEC invasion.
Figure 9B:
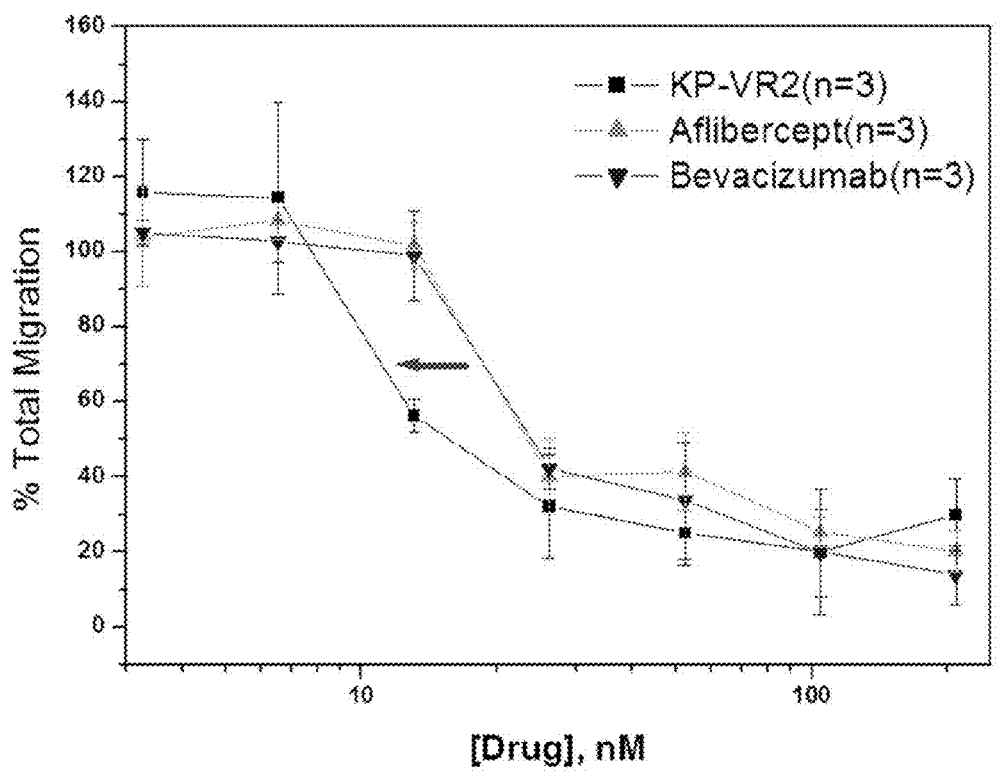

As shown in the FIGS. 9A and 9B, while VEGF induced cell migration and invasion in HUVEC (Lonza), KP-VR2, KP-VR4 (aflibercept) and bevacizumab inhibited the induced cell migration and invasion. The KP-VR2 of the present invention showed higher inhibitory activity than KP-VR4 (aflibercept) and bevacizumab at the same concentration (13 nM). Further, as shown in the Table 3, the IC50 of KP-VR2, KP-VR4 (aflibercept) and bevacizumab were about 11 nM, 20 nM and 21 nM, respectively, which explains that the KP-VR2 has outstanding inhibitory activity to cell invasion.

Example 7-2

Figure 10A:
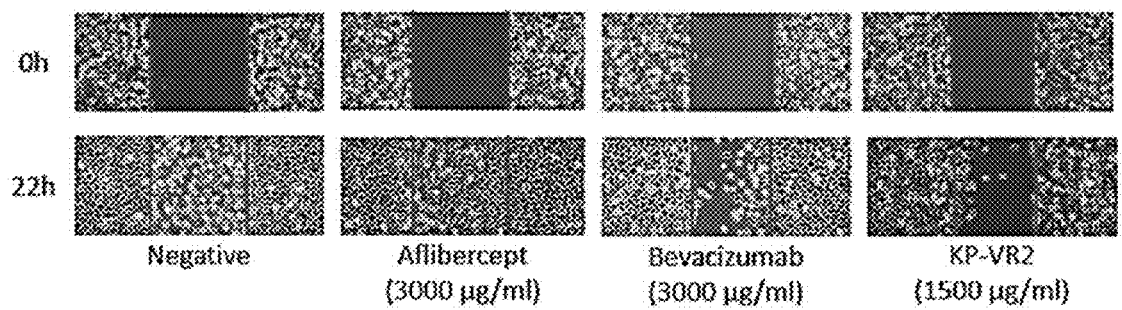
FIGS. 10A and 10B show the effects of the fusion protein of the present invention, aflibercept and bevacizumab on Ea-hy926 migration.
Figure 10B:
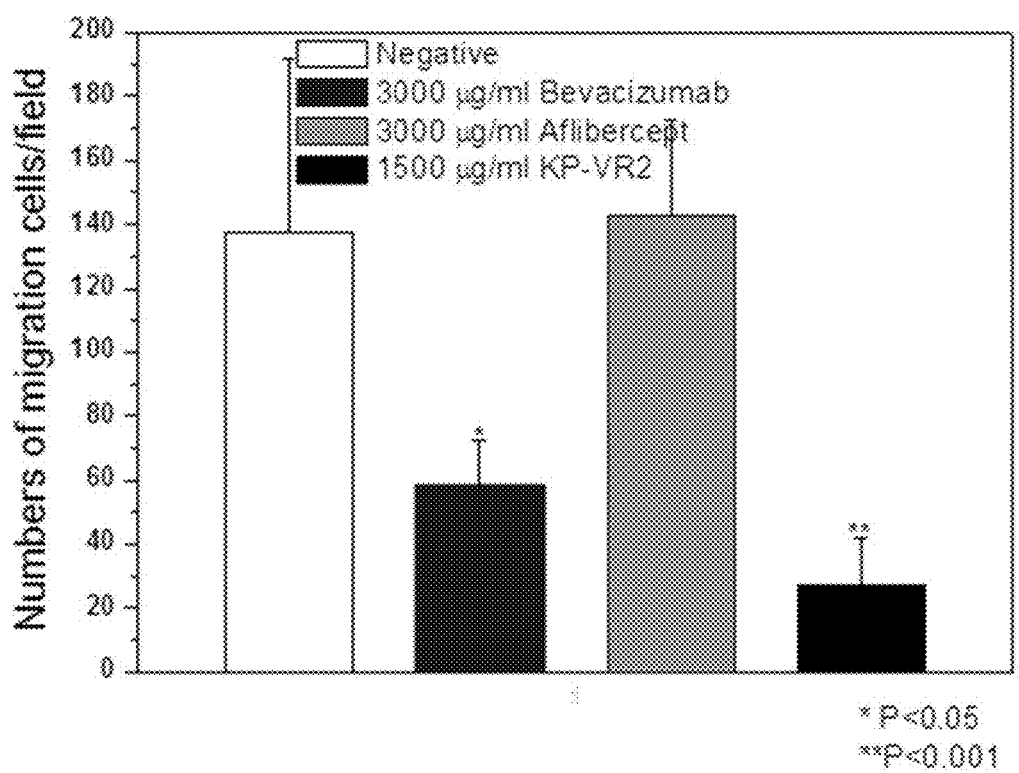

Detection of Cell Invasion Inhibition Induced by the VEGF-A after Treating Ea-Hy926 Cell Line with KP-VR2, KP-VR4 (Aflibercept) or Bevacizumab EA-hy926 cell lines (ATCC CRL-2922™) (3.5×10⁵ cells/ml) were seeded on 96 well plate in DMEM (Dulbecco's Modified Eagle's Medium Sigma) having 0.1% FBS. Next, the plate was treated with the KP-VR2 (1,500 µg/ml), KP-VR4 (aflibercept) (3,000 µg/ml), and bevacizumab (3,000 µg/ml), respectively, at 37° C., 5% CO2 condition for 24 hours. As a negative control, a medium not treated with the fusion proteins was used. The results were shown in FIGS. 10A and 10B. As shown in the FIGS. 10A and 10B, the KP-VR2 of the present invention much effectively inhibited the growth and proliferation of EA-hy926 cells induced by VEGF at lower concentration than KP-VR4 (aflibercept) and bevacizumab.

Example 8

Comparison of Carcinoma Cell Proliferation Inhibitory Abilities Between KP-VR2 and KP-VR4

MTS cell proliferation colorimetric assay was performed for 9 (nine) kinds of carcinoma cell lines to determine the inhibitory ability of KP-VR2 against carcinoma cell division. The Table 4 shows 9 carcinoma cell lines used in this experiment.

TABLE 4

| name | Bio-marker | origins | note |
| --- | --- | --- | --- |
| HT29 | VEGF positive | Human colorectal adenocarcinoma | ATCC HTB-38 ™ |
| LoVo | VEGF positive PLGF positive | Human colorectal adenocarcinoma | ATCC CCL-229 ™ |
| AGS | PLGF positive VEGF positive | Human gastric adenocarcinoma | ATCC CRL-1739 ™ |
| SKUT1b | VEGF positive VEGFR1 positive | Human uterine sarcoma | ATCC HTB-115 ™ |
| Caki-1 | VEGF positive VEGFR1 positive | Renal Clear Cell carcinoma | ATCC HTB-46 ™ |
| Hy-926 | VEGF positive VEGFR1 positive | Human Endothelial | ATCC CRL-2922 ™ |
| HCT 116 | VEGF positive | Human colorectal carcinoma | ATCC CCL-247 ™ |
| PANC 02.03 | VEGF positive | Human Pancreas Adenocarcinoma | ATCC CRL-2553 ™ |
| SW480 | VEGF positive PLGF positive | Human colorectal adenocarcinoma | ATCC CCL-228 ™ |
| PC-3 | VEGF positive PLGF positive | Human prostate adenocarcinoma | ATCC CRL-1435 ™ |

The 9 kinds of carcinoma cell lines, HT-29 (ATCC HTB-38™), LOVO (ATCC CCL-229™), HCT116 (ATCC CCL-247™), SKUT1b (ATCC HTB-115™), Caki-1 (ATCC HTB-46™), AGS (ATCC CRL-1739™), Panc0203 (ATCC CRL-2553™) SW480 (ATCC CCL-228™), and PC-3 (ATCC ORL-1435™) were incubated to reach to full confluency at 37° C., 5% CO2 condition. Next, the carcinoma cell lines were removed and seeded (3×103 cells/well) on RPMI1640 medium (Sigma) comprising 10% FBS. Thereafter, the cell lines were incubated at 37° C. for 24 hours. Next, the medium was substituted with RPMI1640 medium (Sigma) having 0.5% FBS.

Figure 11A:
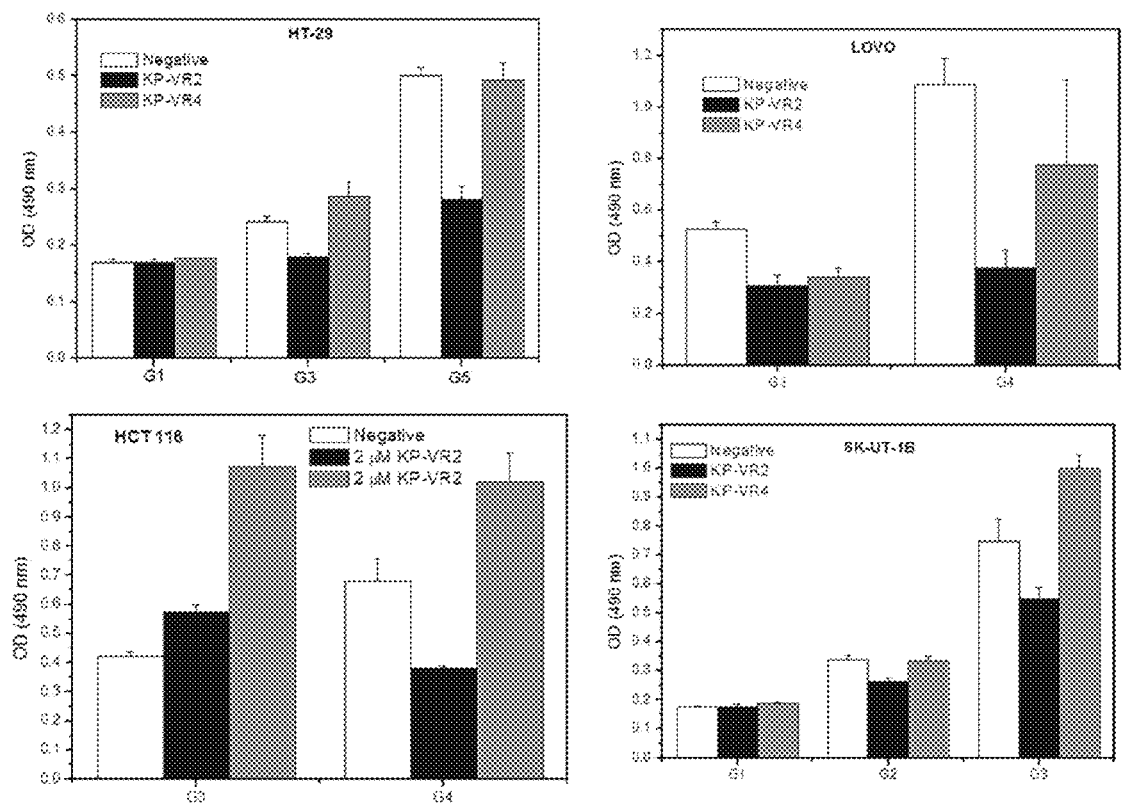
FIGS. 11A and 11B show the ability of the fusion protein of the present invention to inhibit proliferations of 9 (nine) carcinomas, comparing to aflibercept.
Figure 11B:
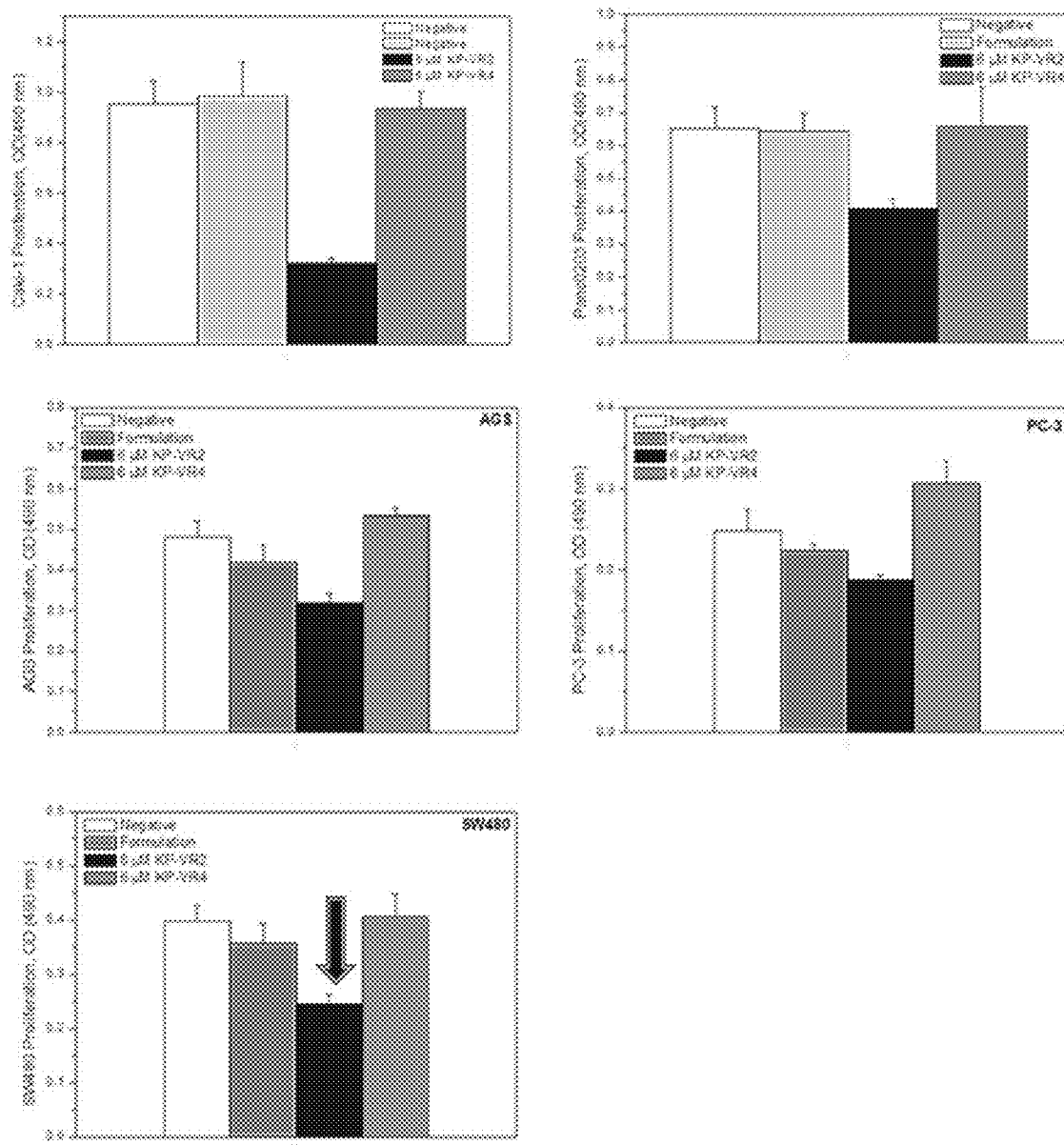

Subsequently, the cell lines were treated with 2, 4 or 6 nM of KP-VR2 or KP-VR4 (aflibercept), and further incubated for 72 hours. The MTS reagent (Qiagen) was added to the plate and absorbance was detected at 490 nm. The results were shown in FIG. 11A, 11B and Table 5. As shown in the FIGS. 11A and 11B, the KP-VR2 of the present invention showed significantly excellent cell division inhibition activity to all carcinoma lines employed in this experiment.

TABLE 5

| Types | test method | in vitro efficacy KP-VR4 | in vitro efficacy KP-VR2 |
| --- | --- | --- | --- |
| EA-hy926 | in vitro efficacy | ~17% growth inhibition | ~33% growth inhibition |
| HT29 | in vitro efficacy | — | ~44% growth inhibition |
| LoVo | in vitro efficacy | ~35% growth inhibition | ~65% growth inhibition |
| HCT116 | in vitro efficacy | — | ~44% growth inhibition |
| SKUT1b | in vitro efficacy | — | ~26% growth inhibition |
| CaKi-1 | in vitro efficacy | — | ~67% growth inhibition |
| PANC0203 | in vitro efficacy | — | ~37% growth inhibition |
| SW480 | in vitro efficacy | — | ~38% growth inhibition |
| AGS | in vitro efficacy | — | ~34% growth inhibition |
| PC-3 | in vitro efficacy | — | ~20% growth inhibition |

Further, as disclosed in the Table 5 (cell growth inhibition activity), the KP-VR2 of the present invention showed highly enhanced effect of cell growth inhibition to the 9 carcinomas targeting VEGF and PlGF.

Example 9

Comparison of Activities of Cell Division Inhibition of KP-VR2 and Aflibercept in Anti-VEGF Resistant Carcinomas and Fibroblast Cell Lines MTS cell growth assay was performed for carcinoma cells and fibroblast cell lines resistant to anti-VEGFA or anti-VEGFR, to assess inhibitory activity of KP-VR2 to carcinoma cell division. The Table 6 shows 4 kinds of carcinoma cell lines and 2 kinds of fibroblast cell lines used in this experiments.

TABLE 6

| types | Biomarker | Origin | note |
| --- | --- | --- | --- |
| CT26 | A model resistant to anti-VEGFR | Mouse Colon carcinoma | ATCC CRL-2638 ™ |
| B16-F10 | A model resistant to FOLFIRY(p38) | Mouse Skin melanoma | ATCC CRL-6475 ™ |
| EL4 | Anti-VEGF-A refractory | Mouse lymphoma | ATCC TIB-39 ™ |
| LCC1 | Anti-VEGF-A refractory | Mouse lung carcinoma | ATCC CRL-1642 ™ |
| NIH3T3 | fibroblast | Mouse embryo fibroblast | KCLB NO21658 |
| Hs27 | fibroblast | Human skin fibroblast | ATCC CRL-1634 ™ |

The 4 kinds of carcinoma cell lines, (EL-4(ATCC TIB-39™), LLC1(ATCC TIB-39™), B16F10 (ATCC CRL-6475™), CT-26 (ATCC CRL-2638™), and PC-3 (ATCC CRL-1435™); and fibroblast cell line NIH3T3 (KCLB No. 21658) and Hs27 (ATCC CRL-1634™) were incubated to reach to full confluency at 37° C., 5% CO2 condition. Next, the carcinoma and fibroblast cell lines were removed and seeded (3×103 cells/well) on RPMI1640 medium (Sigma) comprising 10% FBS. Thereafter, the cell lines were incubated at 37° C. for 24 hours. Then, the medium was substituted with RPMI1640 medium (Sigma) having 0.5% FBS and the cell lines were treated respectively with 2, 4 or 6 nM of the KP-VR2 or KP-VR4 (aflibercept). Subsequently, the treated cell lines were further incubated for 72 hours. Next, the MTS reagent (Qiagen) was added to the plate and absorbance was detected at 490 nm. The results were illustrated in FIG. 12, FIG. 13 and Table 7 (carcinoma and fibroblast cell lines).

TABLE 7

| kinds | test method | KP-VR4 | KP-VR2 |
|---|---|---|---|
| CT26 | in vitro efficacy | — | ~56% growth inhibition |
| B16-F10 | in vitro efficacy | — | ~30% growth inhibition |
| EL4 | in vitro efficacy | ~49% growth inhibition | ~67% growth inhibition |
| LLC1 | in vitro efficacy | ~12% growth inhibition | ~70% growth inhibition |
| NIH3T3 | in vitro efficacy | ~41% growth inhibition | ~52% growth inhibition |
| Hs27 | in vitro efficacy | ~15% growth inhibition | ~25% growth inhibition |

Figure 12:
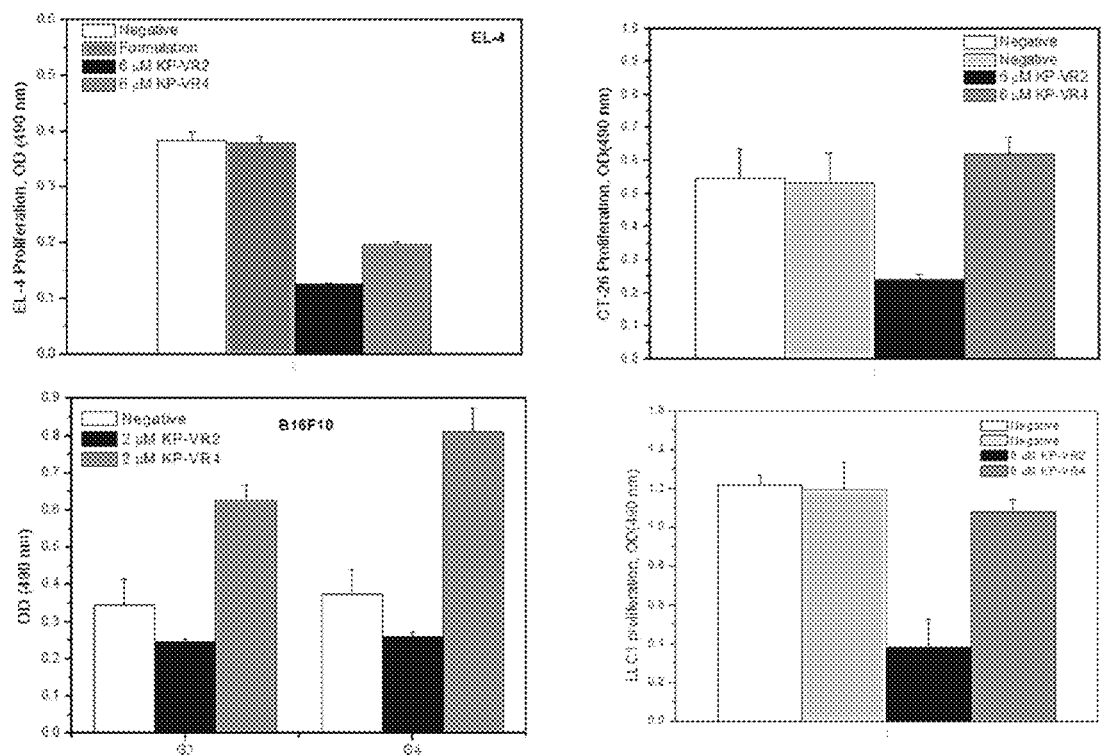
FIGS. 12 and 13 show the inhibitory ability of the fusion protein of the present invention to cell viabilities of anti-VEGF resistant carcinomas and fibroblast, comparing to aflibercept.
Figure 13:
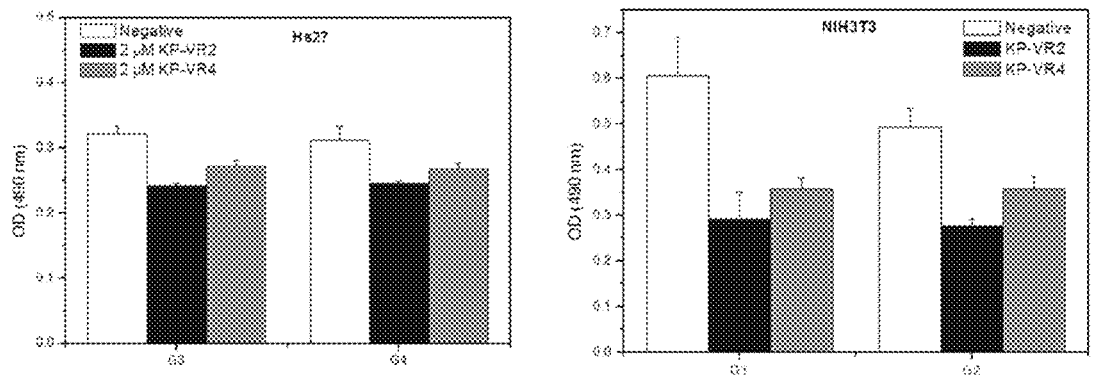

As shown in the FIG. 12, 13 and Table 7, the KP-VR2 of the present invention showed significantly enhanced activity of cell growth inhibition not only for the cancer cells (see Experiment 8), but also for the anti-VEGF/VEGFR resistant carcinoma cell lines (EL-4, LLC1, B16F10 and CT-26) and the fibroblast cell lines (Hs27 and NIH3T3).

Example 10

Comparison of Tumor Growth Inhibition of KP-VR2 and Aflibercept in a Nude Mouse

The various kinds of tumor xenograft models (HT-29, LOVO & SKUT1b) were employed in BALB/c nude mice to perform in vivo experiments for the assessment of tumor growth inhibition activity of KP-VR2.

Experiment 10-1. HT-29 In Vivo Xenograft

Figure 14:
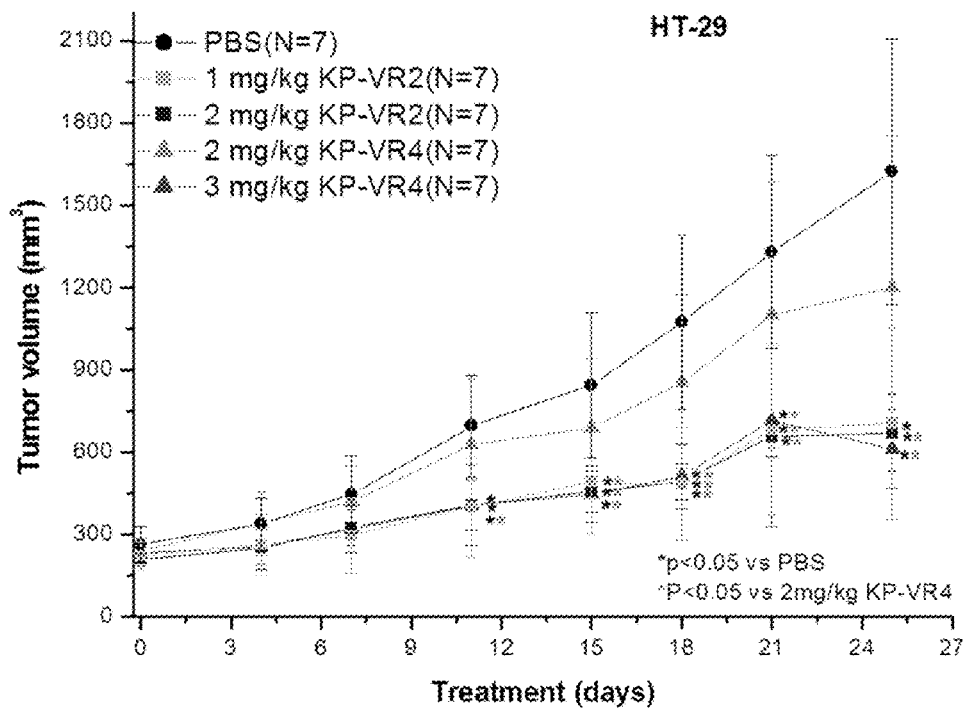
FIGS. 14, 15A, 15B, 16A, 16B, 17A and 17B represent comparison of tumor growth and tumor weights in human cancer models ((HT-29, LOVO and SKUT1B).

HT-29 cells (ATCC HTB-38™) (5×106 cells/0.2 ml) were subcutaneously injected into the back area of a nude mouse (Orient bio, female, 4 week-old). When the volume of tumor became larger than 200 mm³, the KP-VR2 (1 mg/kg or 2 mg/kg) and KP-VR4 (aflibercept) (2 mg/kg or 3 mg/kg) were injected, respectively, into the abdominal cavity of the mouse twice a week, and the same amount of PBS (phosphate buffered saline) was injected into the abdominal cavity of the negative control mouse at the same time and period. The volume of the tumor was measured every 3 to 4 days, and the results were disclosed in FIG. 14. As shown in the FIG. 14, the KP-VR2 of the present invention showed about 40% increased growth inhibition activity for the HT-29 colon cancer cell line at dose of 2 mg/kg, in comparison to the same amount of the aflibercept (KP-VR4). Further, similar effects were observed between the KP-VR2 (1 mg/kg) and the aflibercept (KP-VR4) (3 mg/kg).

Example 10-2

LOVO In Vivo Xenograft

Figure 15A:
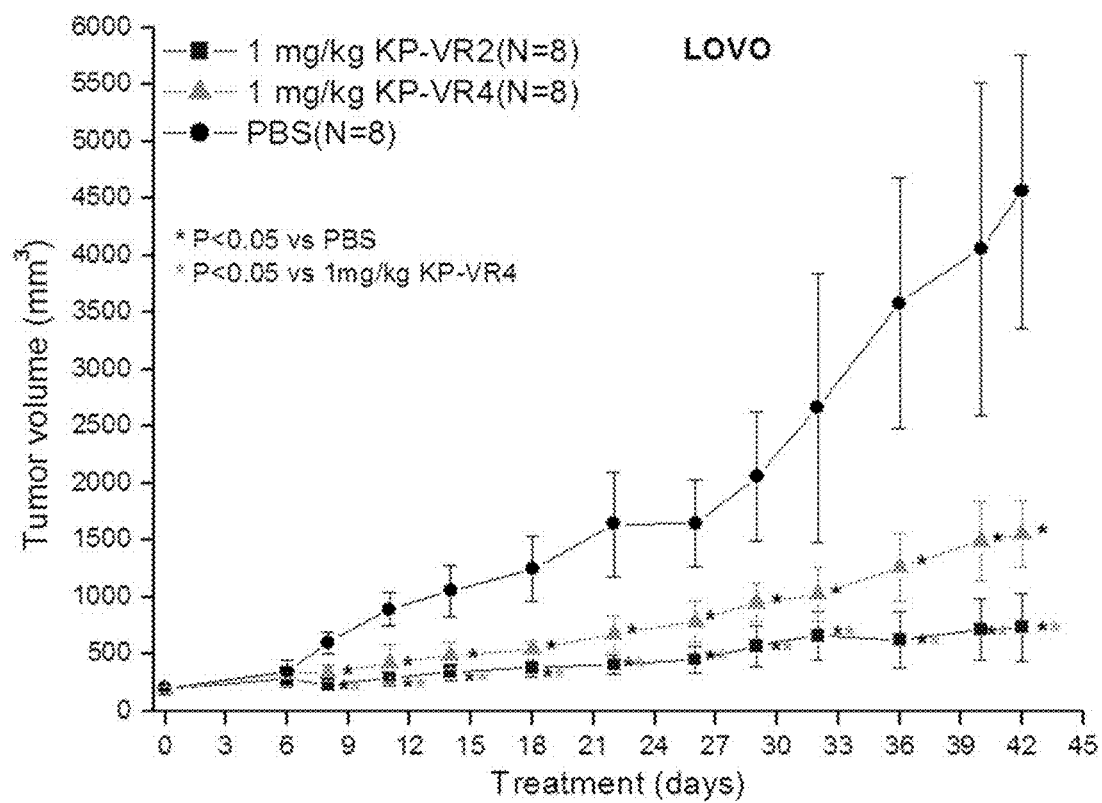
Figure 15B:
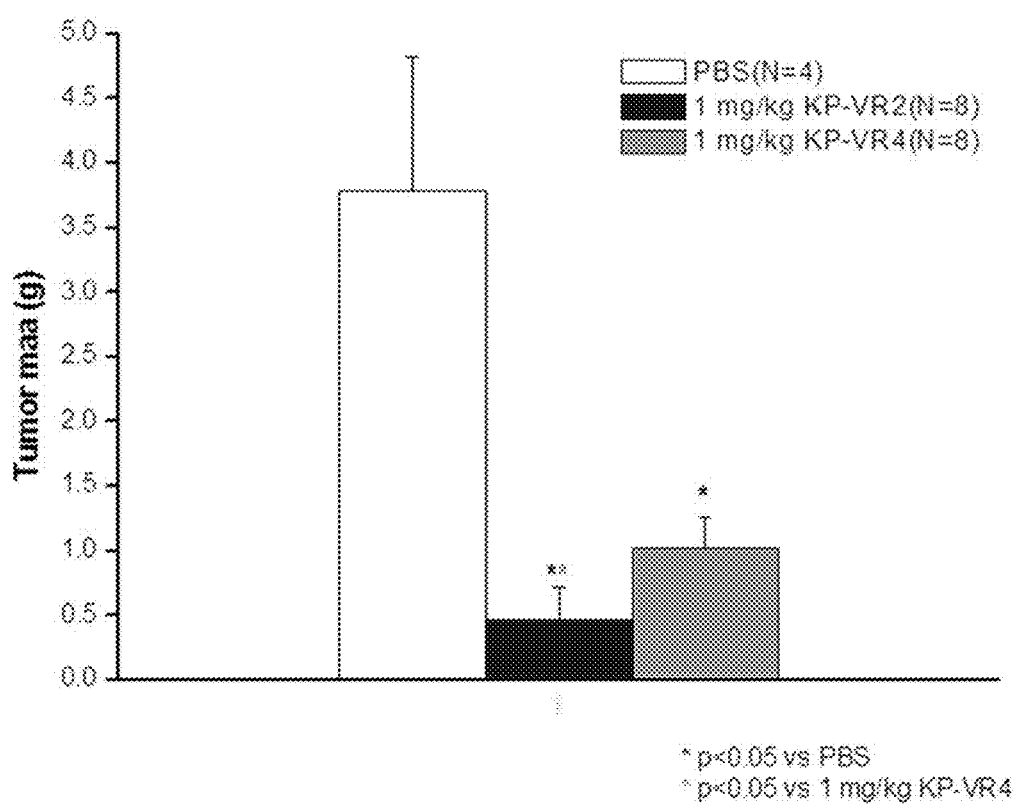

The same experiment as the Example 10-1 was performed using LOVO (ATCC CCL-229™) cell lines instead of HT-29 cell lines. The LOVO cell lines (5×106 cells/0.2 ml) were subcutaneously injected into the back area of a nude mouse (Orient bio, female, 4 week-old). When the volume of the tumor became larger than 200 mm³, KP-VR2 (1 mg/kg) and KP-VR4 (aflibercept) (1 mg/kg) were injected, respectively, into the abdominal cavity of the nude mouse twice a week, and the same amount of PBS (phosphate buffered saline) was injected into the abdominal cavity of the negative control mouse at the same time and period. The volume of the tumor was measured every 3 to 4 days, and the tumor was extracted at the last 42th day to compare the weights. The results were disclosed in FIGS. 15A and 15B. As shown in the FIGS. 15A and 15B, the KP-VR2 of the present invention had 50%~60% increased growth inhibition activity for the rectal cancer cell line (LOVO) at dose of 1 mg/kg, comparing to the same amount of the aflibercept (KP-VR4) (P<0.05). The tumor growth inhibition activity of the KP-VR2 of the present invention was observed from the initial time of injection, and the difference in inhibition activity between the KP-VR2 and the aflibercept (KP-VR4) has increased since the injection. Further, the injection of the present KP-VR2 resulted in about 50% reduced tumor weight, comparing to the aflibercept at the same injection dose.

Example 10-3

SKUT1B In Vivo Xenograft

Figure 16A:
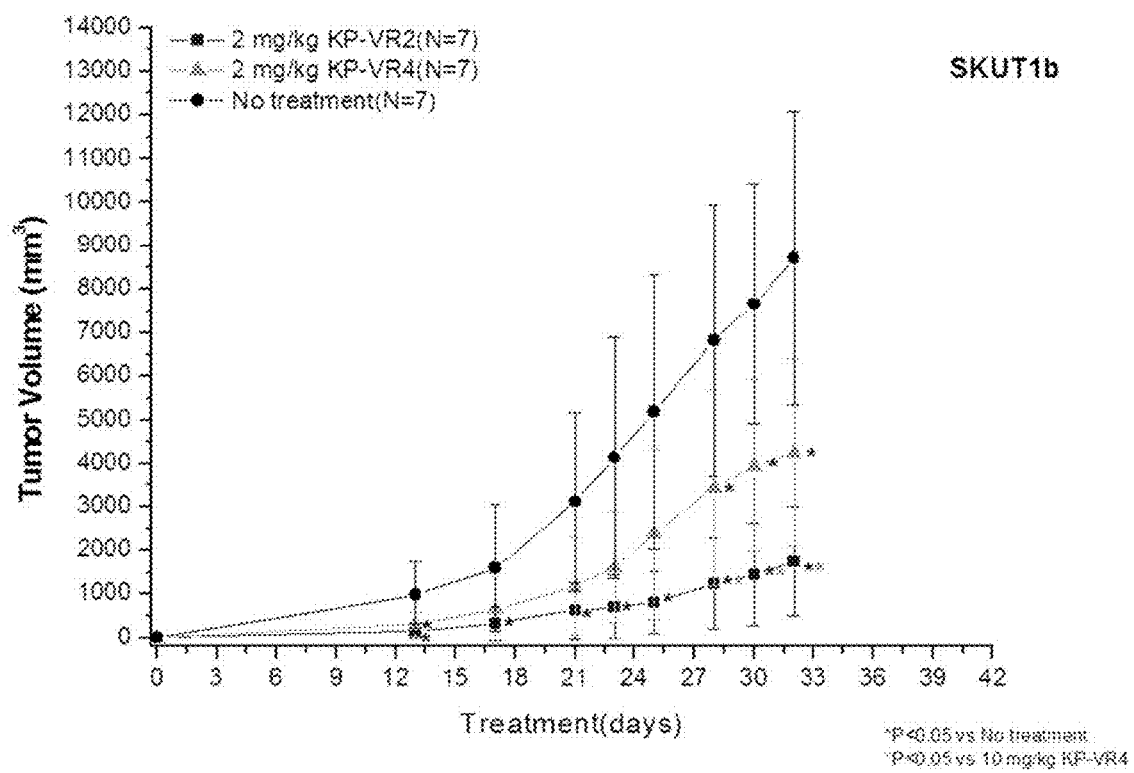
Figure 16B:
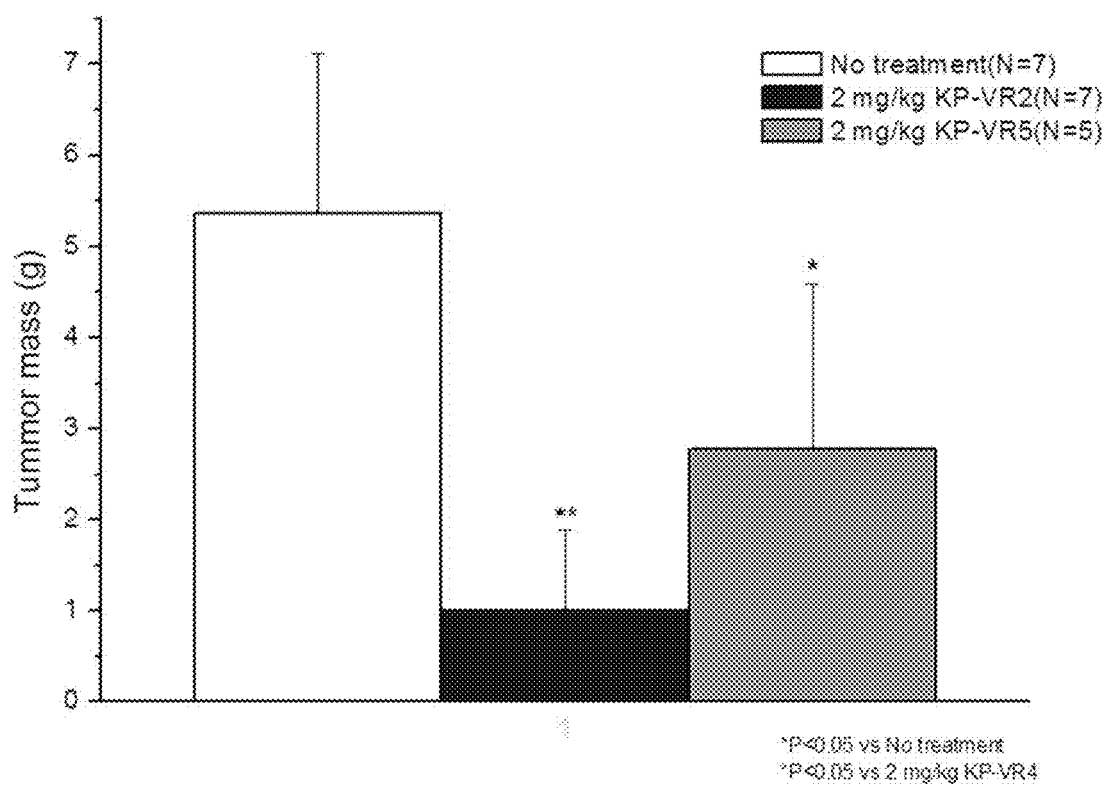
Figure 17A:
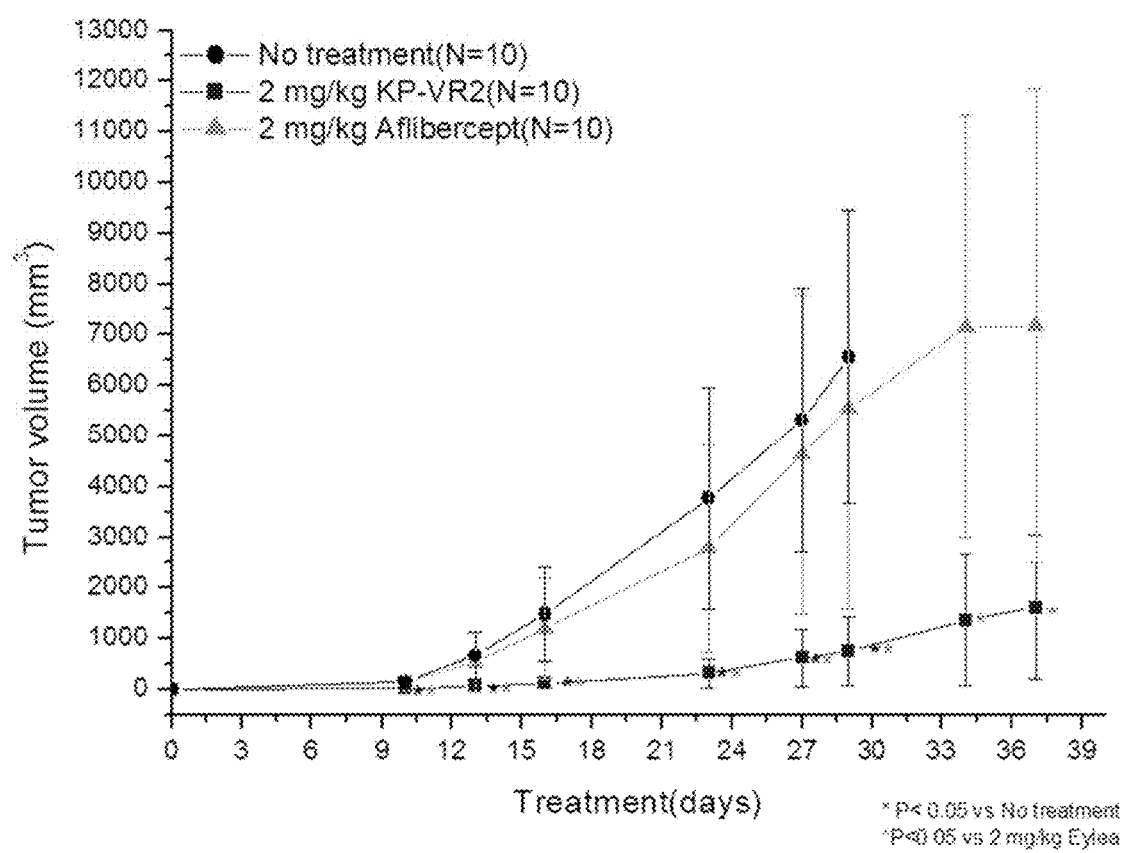
Figure 17B:
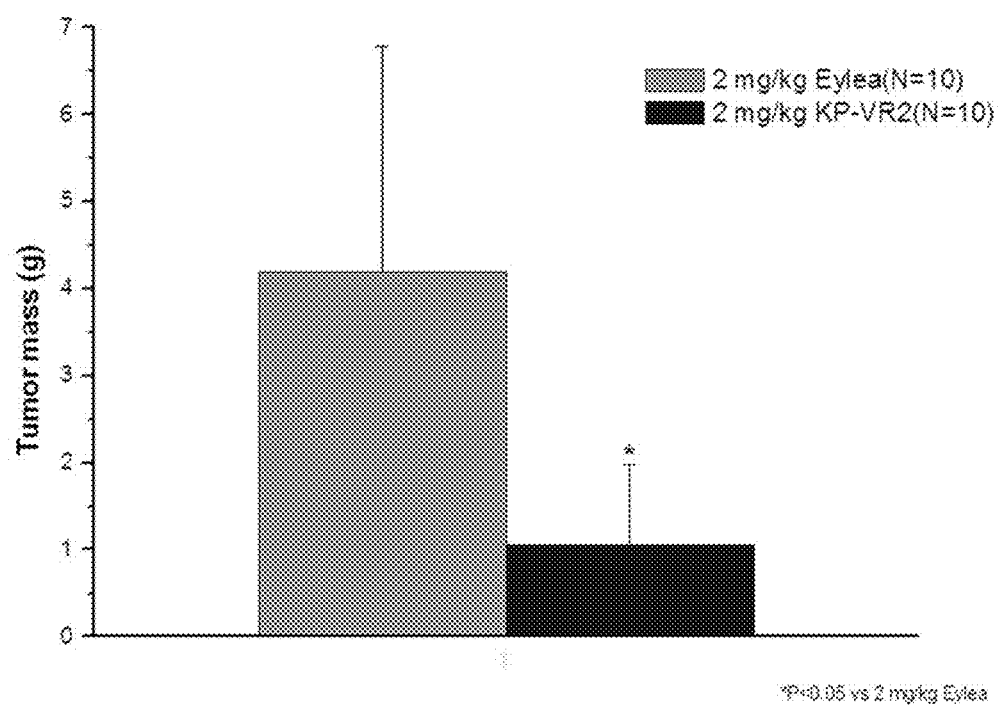
Figure 18:
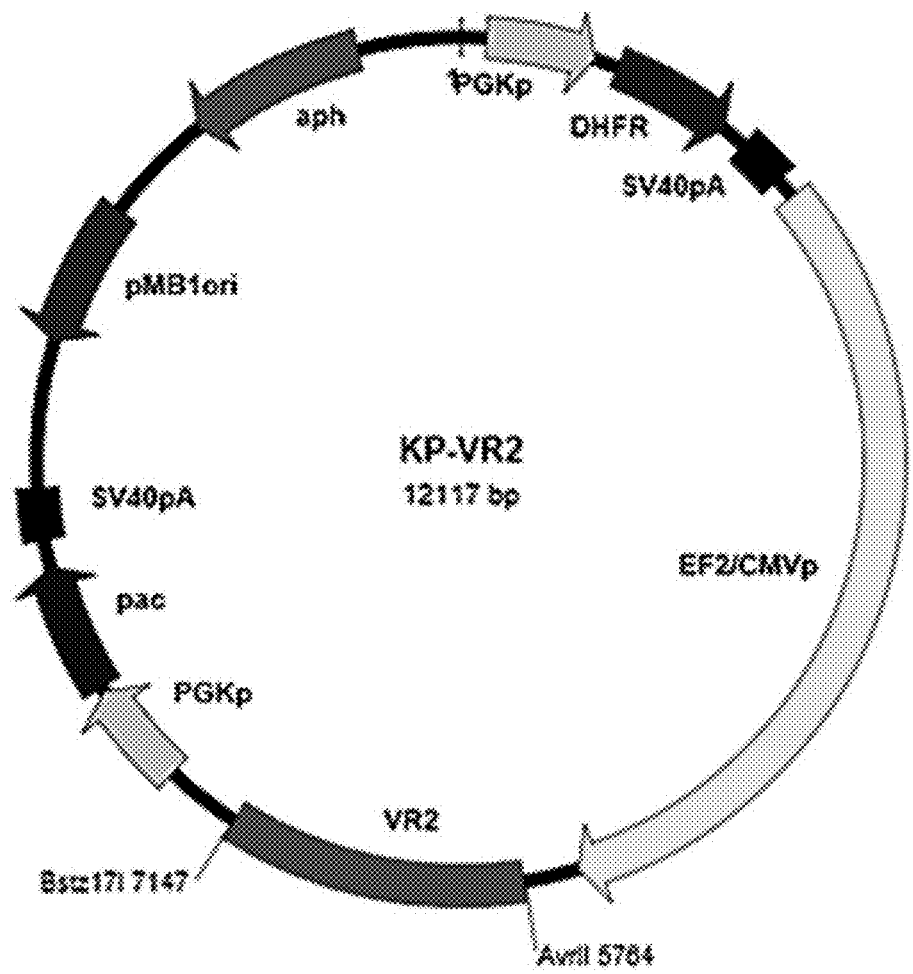
FIG. 18 shows the recombinant expression vector for KP-VR2.
Figure 19:
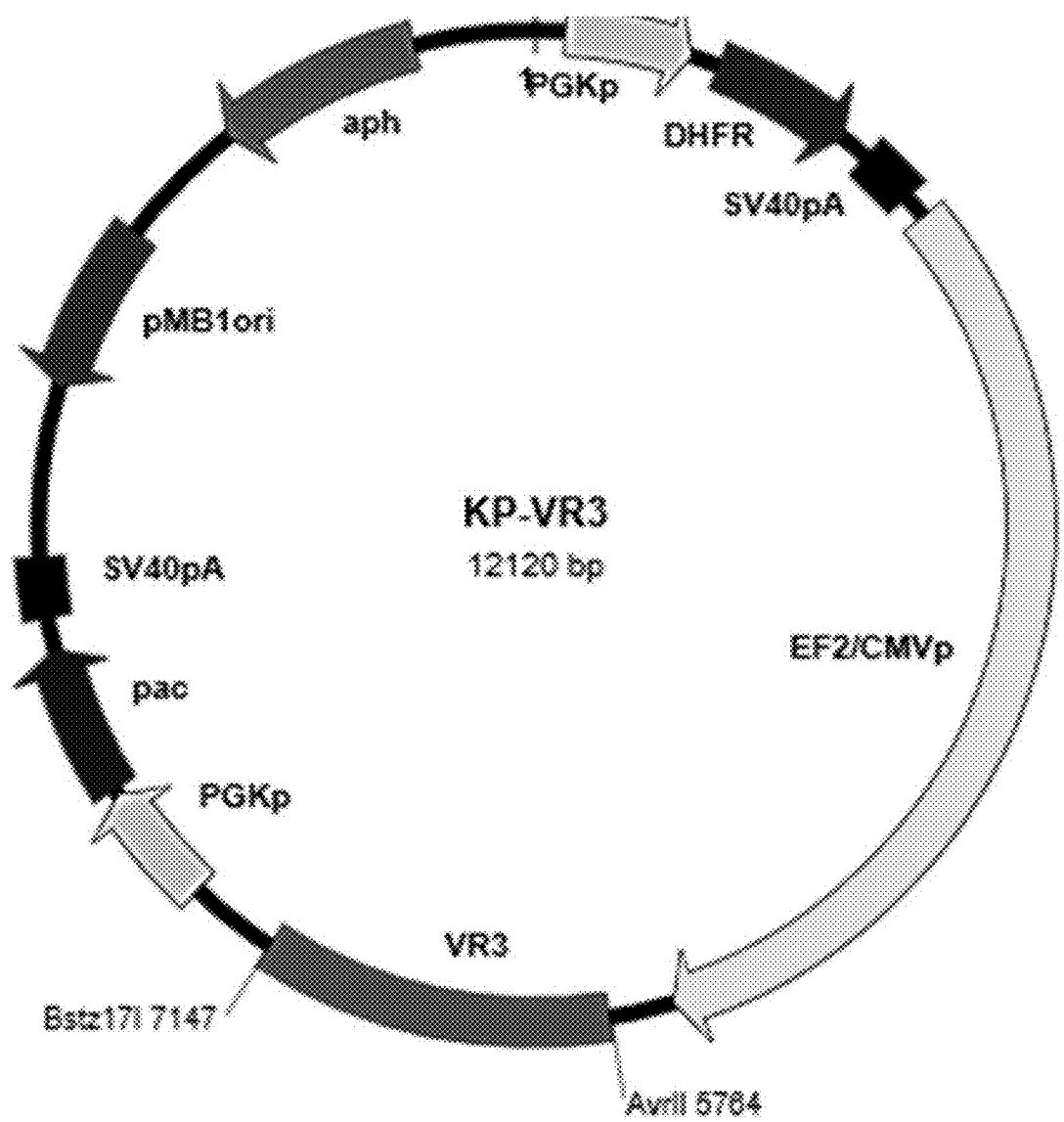
FIG. 19 shows the recombinant expression vector for KP-VR3.

The uterus cancer SKUT1B cell line (ATCC HTB-115™), which is a VEGFR1-positive cell line, was injected into the nude mouse. The SKUT1B cell lines (1×107 cells/0.2 ml) were subcutaneously injected into the back area of the nude mouse, and the KP-VR2 (2 mg/kg) and KP-VR4 (aflibercept) (2 mg/kg) were injected, respectively, into the abdominal cavity of the nude mouse twice a week from 1 day to 32 day after the injection. The same amount of PBS (phosphate buffered saline) was injected into the abdominal cavity of the negative control mouse at the same time and period. The volume of the tumor was observed every 3 to 4 days, and the tumor was extracted at the last 37th day to compare the weights of tumors. The results were disclosed in FIGS. 16A and 16B. As shown in the FIGS. 16A and 16B, the KP-VR2 of the present invention had 60%~70% increased growth inhibition activity for the cell lines used in this experiment at dose of 2 mg/kg, comparing to the same amount of the aflibercept (KP-VR4) (P<0.05). Further, the injection of the present KP-VR2 resulted in about 70% reduced tumor weight, comparing to the aflibercept at the same injection dose.

INDUSTRIAL APPLICABILITY

As described above, the (VEGFR) fusion protein of the present invention comprises (a) a Fc domain of IgG1, wherein two heavy chains are linked by disulfide bond, and (b) four immunoglobulin domain2s of the VEGFR1, wherein two immunoglobulin domain2s are sequentially fused to each heavy chain of the Fc domain of (a). Accordingly, the present invention enables to provide a pharmaceutical composition for treating cancers and/or ocular diseases caused by angiogenesis.

The invention claimed is:

1. A fusion protein that binds to vascular endothelial growth factor (VEGF), comprising
   (a) an Fc domain of IgG1, wherein two heavy chains of the Fc domain are linked by a disulfide bond; and
   (b) four immunoglobulin domain2s of VEGFR1,
   and wherein one of the immunoglobulin domain2s of VEGFR1 and another immunoglobulin domain2 of VEGFR1 are sequentially fused to each heavy chain of the Fc domain of (a).

2. An isolated nucleic acid molecule encoding a fusion protein, wherein the fusion protein comprises,
   (a) an Fc domain of IgG1, wherein two heavy chains of the Fc domain are linked by a disulfide bond; and
   (b) four immunoglobulin domain2s of VEGFR1,
   wherein one of the immunoglobulin domain2s of VEGFR1and another immunoglobulin domain2 of VEGFR1 are sequentially fused to each heavy chain of the Fc domain of (a),
   and wherein the isolated nucleic acid molecule comprises the nucleic acid sequence encoding the Fc domain and the four immunoglobulin domain2s of the VEGFR1.

3. A recombinant expression vector comprising the isolated nucleic acid molecule of claim 2.

4. The recombinant expression vector of claim 3, which is any one selected from the group consisting of YAC (yeast artificial chromosome), YEp (yeast episomal plasmid), YIp (yeast integrative plasmid) and recombinant virus.

5. A host cell comprising the recombinant expression vector of claim 4.

6. The host cell of claim 5, which is any one selected from the group consisting of bacteria, yeast, insect cell and mammalian cell.

7. The host cell of claim 6, wherein the mammalian cell is a CHO (chinese hamster ovary) cell.

8. A method for producing a fusion protein of immunoglobulin-like domain binding to VEGF, which comprises,
   (a) incubating the host cell of claim 5 under conditions for the production of a polypeptide; and
   (b) recovering the polypeptide produced in the above (a).

9. A fusion protein of immunoglobulin-like domain produced according to the method of claim 8.

10. A pharmaceutical composition for treating angiogenic tumor, which comprises the fusion protein of claim 1 as a pharmacologically active ingredient and pharmaceutically acceptable excipients.

11. The pharmaceutical composition for treating angiogenic tumor of claim 10, wherein the tumor is colon cancer, pancreatic cancer, rectal cancer, stomach cancer, kidney cancer, prostate cancer, uterine sarcoma, leukemia, or skin cancer.

12. A pharmaceutical composition for treating angiogenic ocular disease, which comprises the fusion protein of claim 1 as a pharmacologically active ingredient and pharmaceutically acceptable excipients.

13. The pharmaceutical composition for treating angiogenic ocular disease of claim 12, wherein the ocular disease is senile macular degeneration, exudative senile macular degeneration, choroidal neovascularization, pathologic myopia, diabetic retinopathy, diabetic macular edema, retinal vascular occlusions, retinopathy of prematurity or angiogenic glioma.

14. A method for producing a fusion protein of immunoglobulin-like domain binding to VEGF, which comprises,
   (a) incubating the host cell of claim 6 under conditions for the production of a polypeptide; and
   (b) recovering the polypeptide produced in the above (a).

15. A fusion protein of immunoglobulin-like domain produced according to the method of claim 14.

16. A method for producing a fusion protein of immunoglobulin-like domain binding to VEGF, which comprises,
   (a) incubating the host cell of claim 7 under conditions for the production of a polypeptide; and
   (b) recovering the polypeptide produced in the above (a).

17. A fusion protein of immunoglobulin-like domain produced according to the method of claim 16.

\* \* \* \* \*

SEQUENCE LISTING

<160> NUMBER OF SEQ ID NOS: 3

<210> SEQ ID NO 1
<211> LENGTH: 102
<212> TYPE: PRT
<213> ORGANISM: Artificial Sequence

```
<220> FEATURE:
<223> OTHER INFORMATION: VEGFR1 domain 2

<400> SEQUENCE: 1

Ser Asp Thr Gly Arg Pro Phe Val Glu Met Tyr Ser Glu Ile Pro Glu
  1               5                  10                  15

Ile Ile His Met Thr Glu Gly Arg Glu Leu Val Ile Pro Cys Arg Val
             20                  25                  30

Thr Ser Pro Asn Ile Thr Val Thr Leu Lys Lys Phe Pro Leu Asp Thr
         35                  40                  45

Leu Ile Pro Asp Gly Lys Arg Ile Ile Trp Asp Ser Arg Lys Gly Phe
     50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                 85                  90                  95

Gln Thr Asn Thr Ile Ile
                100

<210> SEQ ID NO 2
<211> LENGTH: 233
<212> TYPE: PRT
<213> ORGANISM: Artificial Sequence
<220> FEATURE:
<223> OTHER INFORMATION: Human IgG1 Fc region

<400> SEQUENCE: 2

Ala Glu Pro Lys Ser Cys Asp Lys Thr His Thr Cys Pro Pro Cys Pro
  1               5                  10                  15

Ala Pro Glu Leu Leu Gly Gly Pro Ser Val Phe Leu Phe Pro Pro Lys
             20                  25                  30

Pro Lys Asp Thr Leu Met Ile Ser Arg Thr Pro Glu Val Thr Cys Val
         35                  40                  45

Val Val Asp Val Ser His Glu Asp Pro Glu Val Lys Phe Asn Trp Tyr
     50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
                100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
```

```
<210> SEQ ID NO 3
<211> LENGTH: 103
<212> TYPE: PRT
<213> ORGANISM: Artificial Sequence
<220> FEATURE:
<223> OTHER INFORMATION: VEGFR2-D3

<400> SEQUENCE: 3

Asp Val Val Leu Ser Pro Ser His Gly Ile Glu Leu Ser Val Gly Glu
 1               5                  10                  15

Lys Leu Val Leu Asn Cys Thr Ala Arg Thr Glu Leu Asn Val Gly Ile
             20                  25                  30

Asp Phe Asn Trp Glu Tyr Pro Ser Ser Lys His Gln His Lys Lys Leu
         35                  40                  45

Val Asn Arg Asp Leu Lys Thr Gln Ser Gly Ser Glu Met Lys Lys Phe
     50                  55                  60

Leu Ser Thr Leu Thr Ile Asp Gly Val Thr Arg Ser Asp Gln Gly Leu
 65                  70                  75                  80

Tyr Thr Cys Ala Ala Ser Ser Gly Leu Met Thr Lys Lys Asn Ser Thr
                 85                  90                  95

Phe Val Arg Val His Glu Lys
            100
```